(12) United States Patent
Pursell et al.

(10) Patent No.: US 6,890,888 B2
(45) Date of Patent: May 10, 2005

(54) CONTROLLED RELEASE AGRICULTURAL PRODUCTS AND PROCESSES FOR MAKING SAME

(75) Inventors: Taylor Pursell, Birmingham, AL (US); Arthur R. Shirley, Jr., Florence, AL (US); Keith D. Cochran, Killen, AL (US); Timothy G. Holt, Florence, AL (US); Gregory S. Pedeen, Killen, AL (US)

(73) Assignee: NFT Industries, LLC, Birmingham, AL (US)

( * ) Notice: Subject to any disclaimer, the term of this patent is extended or adjusted under 35 U.S.C. 154(b) by 159 days.

(21) Appl. No.: 09/895,876

(22) Filed: Jul. 2, 2001

(65) Prior Publication Data

US 2002/0098983 A1 Jul. 25, 2002

Related U.S. Application Data

(60) Provisional application No. 60/254,178, filed on Dec. 11, 2000, and provisional application No. 60/216,132, filed on Jul. 3, 2000.

(51) Int. Cl.⁷ ........................ A01N 25/12; A01N 25/34; C05G 5/00
(52) U.S. Cl. ................ 504/323; 504/359; 504/367; 71/64.11; 514/964
(58) Field of Search ................ 504/323, 359, 504/367; 71/64.11; 514/964

(56) References Cited

U.S. PATENT DOCUMENTS

| | | |
|---|---|---|
| 33,983 A | 12/1861 | Cauhaupe |
| 93,607 A | 8/1869 | Fish |
| 371,630 A | 10/1887 | Rose et al. |
| 879,877 A | 2/1908 | Kennedy |
| 1,783,694 A | 12/1930 | Blumenberg et al. |
| 1,944,788 A | 1/1934 | Benz |
| 1,993,434 A | 3/1935 | Champney |
| 2,005,365 A | 6/1935 | Giacinto |
| 2,019,824 A | 11/1935 | Liehr et al. |
| 2,032,608 A | 3/1936 | Antrim |

(Continued)

FOREIGN PATENT DOCUMENTS

| | | |
|---|---|---|
| EP | 0068287 | 1/1983 |
| GB | 2227245 | 7/1990 |
| JP | 63117984 | 5/1988 |

OTHER PUBLICATIONS

Meisinger, A.C., Perlite, Bureau of Mines Bulletin 675, Mineral Facts and Problems, 1985 ed.
Bolen, W.P., Perlite, Minerals Yearbook, Metals and Minerals, vol. 1, U.S. Dept. of the Interior, U.S. Geological Survey, 1995.

*Primary Examiner*—S. Mark Clardy
(74) *Attorney, Agent, or Firm*—Paul E. White, Jr.; Manelli Denison & Selter PLLC

(57) ABSTRACT

A controlled release agricultural absorbent based product including particles of an absorbent material containing capillaries/voids between 10–200 microns in cross-sectional diameter which is impregnated in an amount of 40–95% of the capillaries/voids volume with an agriculturally beneficial material selected from the group consisting of fertilizers, insecticides, herbicides and fungicides, being produced by a process including steps of 1) introducing water to particles of absorbent material to result in absorption of water within the absorbent material, 2) heating the absorbent particles and water to transform the water within the absorbent particles to steam, 3) introducing the heated absorbent particles to an agriculturally beneficial material in aqueous solution to essentially saturate the absorbent particles with the agriculturally beneficial material, 4) granulating the combination of agriculturally beneficial material and saturated absorbent particles to solidify and harden the mixture, resulting in the agglomeration of absorbent particles into granules, and 5) drying the granules.

146 Claims, 6 Drawing Sheets

U.S. PATENT DOCUMENTS

| | | |
|---|---|---|
| 2,044,861 A | 6/1936 | Sindeh |
| 2,092,100 A | 9/1937 | Waynick |
| 2,165,592 A | 7/1939 | Treeland |
| 2,498,480 A | 2/1950 | Bierlich |
| 2,502,996 A | 4/1950 | Rohner et al. |
| 2,618,546 A | 11/1952 | Davenport |
| 2,669,510 A | 2/1954 | Dresser |
| 2,695,840 A | 11/1954 | Leppia |
| 2,714,553 A | 8/1955 | Bibb et al. |
| 2,751,713 A | 6/1956 | Abramitis |
| 2,766,283 A | 10/1956 | Darden |
| 2,779,670 A | 1/1957 | Burkett |
| 2,806,773 A | 9/1957 | Pole |
| 2,810,710 A | 10/1957 | Long |
| 2,816,826 A | 12/1957 | Brennan |
| 2,867,521 A | 1/1959 | Jeffreys |
| 2,904,424 A | 9/1959 | Chapman et al. |
| 2,931,140 A | 4/1960 | Laffler et al. |
| 3,017,720 A | 1/1962 | Busch |
| 3,030,734 A | 4/1962 | Brickey |
| 3,057,713 A | 10/1962 | Gessler |
| 3,059,379 A | 10/1962 | Attoe |
| 3,060,012 A | 10/1962 | Pavek |
| 3,075,836 A | 1/1963 | Jackson |
| 3,076,700 A | 2/1963 | Renner |
| 3,137,631 A | 6/1964 | Soloway |
| 3,150,955 A | 9/1964 | Smith |
| 3,161,497 A | 12/1964 | Amburn |
| 3,172,752 A | 3/1965 | Pierce |
| 3,174,845 A | 3/1965 | Macarthur |
| 3,192,031 A | 6/1965 | Zaayenga |
| 3,198,761 A | 8/1965 | O'Donnell |
| 3,218,149 A | 11/1965 | Sproull et al. |
| 3,219,432 A | 11/1965 | Schafer et al. |
| 3,220,824 A | 11/1965 | Church |
| 3,248,255 A | 4/1966 | Belasco et al. |
| 3,252,785 A | 5/1966 | Hoblit |
| 3,259,501 A | 7/1966 | Ulrey |
| 3,264,089 A | 8/1966 | Hansen |
| 3,269,824 A | 8/1966 | Aswell |
| 3,288,707 A | 11/1966 | Hurwitz et al. |
| 3,336,129 A | 8/1967 | Herrett et al. |
| 3,369,884 A | 2/1968 | Barron |
| 3,425,971 A | 2/1969 | Gugliemelli et al. |
| 3,497,345 A | 2/1970 | Duyfjes |
| 3,502,458 A | 3/1970 | Schenk |
| 3,558,299 A | 1/1971 | Baskin |
| 3,640,696 A | 2/1972 | Goldmann |
| 3,645,714 A | 2/1972 | Heming et al. |
| 3,661,815 A | 5/1972 | Smith |
| 3,672,945 A | 6/1972 | Taylor |
| 3,697,371 A | 10/1972 | Schleicher et al. |
| 3,808,093 A | 4/1974 | Hedstrom |
| 3,878,304 A | 4/1975 | Moore |
| 3,900,378 A | 8/1975 | Yen et al. |
| 3,929,446 A | 12/1975 | Trocino |
| 3,932,322 A | 1/1976 | Duchane |
| 3,940,257 A | 2/1976 | Sherwin et al. |
| 3,953,191 A | 4/1976 | Barton |
| 3,960,580 A | 6/1976 | Stierli et al. |
| 3,963,118 A | 6/1976 | Ferguson |
| 3,997,319 A | 12/1976 | Ott |
| 3,997,484 A | 12/1976 | Weaver et al. |
| 4,009,020 A | 2/1977 | Starke et al. |
| 4,010,308 A | 3/1977 | Wiczer |
| 4,014,135 A | 3/1977 | Greenbaum |
| 4,014,917 A | 3/1977 | Carter |
| 4,019,889 A | 4/1977 | Kealy |
| 4,052,167 A | 10/1977 | Goff |
| 4,058,124 A | 11/1977 | Yen et al. |
| 4,062,855 A | 12/1977 | Allan et al. |
| 4,067,716 A | 1/1978 | Sterrett |
| 4,074,997 A | 2/1978 | Cohen |
| 4,098,006 A | 7/1978 | Maffet |
| 4,099,336 A | 7/1978 | Maffet |
| 4,121,349 A | 10/1978 | Maffet |
| 4,126,445 A | 11/1978 | Allan et al. |
| 4,145,202 A | 3/1979 | Grodin et al. |
| 4,157,696 A | 6/1979 | Carlberg |
| 4,160,342 A | 7/1979 | Dryer |
| 4,168,962 A | 9/1979 | Lambeth |
| 4,175,355 A | 11/1979 | Dedolph |
| 4,196,543 A | 4/1980 | Dedolph |
| 4,218,234 A | 8/1980 | Nadasy et al. |
| 4,241,537 A | 12/1980 | Wood |
| 4,245,396 A | 1/1981 | Maffet |
| 4,246,018 A | 1/1981 | Wahlberg |
| 4,252,555 A | 2/1981 | Nadasy et al. |
| 4,252,556 A | 2/1981 | Nadasy et al. |
| 4,274,860 A | 6/1981 | Firth |
| 4,280,830 A | 7/1981 | Ferguson et al. |
| 4,321,076 A | 3/1982 | Firth |
| 4,328,025 A | 5/1982 | Whitcomb |
| 4,351,754 A | 9/1982 | Dupre |
| 4,369,197 A | 1/1983 | Basel et al. |
| 4,378,238 A | 3/1983 | Goertz |
| 4,388,352 A | 6/1983 | Allan et al. |
| 4,402,725 A | 9/1983 | Heller et al. |
| 4,404,013 A | 9/1983 | Rainbow |
| 4,409,925 A | 10/1983 | Brundrett et al. |
| 4,455,161 A | 6/1984 | Cohen et al. |
| 4,579,579 A | 4/1986 | Kerr |
| 4,657,582 A * | 4/1987 | Huber .................. 71/121 |
| 4,698,443 A | 10/1987 | Young et al. |
| 4,704,160 A | 11/1987 | McVey et al. |
| 4,710,366 A | 12/1987 | Astley et al. |
| 4,711,659 A | 12/1987 | Moore |
| 4,753,035 A | 6/1988 | Ryan et al. |
| 4,756,738 A | 7/1988 | Detroit |
| 4,767,440 A | 8/1988 | Salac |
| 4,777,763 A | 10/1988 | Shannon et al. |
| 4,803,803 A | 2/1989 | Moffet |
| 4,808,391 A | 2/1989 | Leavitt et al. |
| 4,813,997 A | 3/1989 | Kinnersley et al. |
| 4,820,361 A | 4/1989 | McKenzie et al. |
| 4,824,473 A | 4/1989 | McVey et al. |
| 4,867,779 A | 9/1989 | Meunier et al. |
| 4,889,747 A * | 12/1989 | Wilson .................. 427/221 |
| 4,906,273 A | 3/1990 | Wright |
| 4,906,276 A | 3/1990 | Hughes |
| 4,923,506 A * | 5/1990 | Huber et al. .................. 71/121 |
| 4,927,447 A | 5/1990 | Youssef et al. |
| 4,927,455 A | 5/1990 | Hotta et al. |
| 4,943,308 A | 7/1990 | Vanmarcke et al. |
| 4,975,108 A | 12/1990 | Pruitt |
| 5,022,182 A | 6/1991 | Anderson |
| 5,099,605 A | 3/1992 | Moffet |
| 5,102,440 A | 4/1992 | Gallant et al. |
| 5,106,405 A | 4/1992 | Goto |
| 5,114,457 A | 5/1992 | Evans |
| 5,114,459 A | 5/1992 | Peters et al. |
| 5,174,806 A | 12/1992 | Masuda |
| 5,188,654 A | 2/1993 | Manalastas et al. |
| 5,190,764 A | 3/1993 | Chiba et al. |
| 5,238,841 A | 8/1993 | Kinnersley et al. |
| 5,256,181 A | 10/1993 | Manalastas et al. |
| 5,256,300 A | 10/1993 | Cockett et al. |
| 5,264,471 A | 11/1993 | Chmelir |
| 5,300,135 A | 4/1994 | Hudson et al. |
| 5,312,474 A | 5/1994 | Iijima |
| 5,317,834 A | 6/1994 | Anderson |

| | | |
|---|---|---|
| 5,320,961 A | 6/1994 | Zhong et al. |
| 5,405,425 A | 4/1995 | Pieh et al. |
| 5,423,897 A | 6/1995 | Hudson et al. |
| 5,435,821 A | 7/1995 | Duvdevani et al. |
| 5,466,274 A | 11/1995 | Hudson et al. |
| 5,501,720 A | 3/1996 | Buchholz |
| 5,512,079 A | 4/1996 | Jahnke et al. |
| 5,518,517 A | 5/1996 | Jahnke et al. |
| 5,529,597 A | 6/1996 | Iijima |
| RE35,320 E | 8/1996 | Kinnersley et al. |
| 5,567,220 A | 10/1996 | Thorpe et al. |
| 5,642,587 A | 7/1997 | Janes et al. |
| 5,651,213 A | 7/1997 | Egan |
| 5,672,359 A | 9/1997 | Digenis et al. |
| 5,676,727 A | 10/1997 | Radlein et al. |
| 5,693,119 A | 12/1997 | Lynch et al. |
| 5,718,972 A | 2/1998 | Murase et al. |
| 5,725,630 A | 3/1998 | Roberts et al. |
| 5,736,595 A | 4/1998 | Gunther et al. |
| 5,739,081 A * | 4/1998 | Lloyd et al. ................ 504/116 |
| 5,741,521 A | 4/1998 | Knight et al. |
| 5,746,024 A | 5/1998 | Rice et al. |
| 5,750,130 A | 5/1998 | Ferrell et al. |
| 5,761,847 A | 6/1998 | Ito et al. |
| 5,794,550 A | 8/1998 | Chadwick |
| 5,795,377 A | 8/1998 | Tanner et al. |
| 5,801,116 A | 9/1998 | Cottrell et al. |
| 5,806,445 A | 9/1998 | Decker |
| 5,807,364 A | 9/1998 | Hansen |
| 5,849,060 A | 12/1998 | Diping et al. |
| 5,852,896 A | 12/1998 | Flasch |
| 5,856,370 A | 1/1999 | Chmelir |
| 5,866,678 A | 2/1999 | Kajikawa et al. |
| 5,876,739 A * | 3/1999 | Turnblad et al. ............ 424/408 |
| 5,876,990 A | 3/1999 | Reddy et al. |
| 5,888,930 A | 3/1999 | Smith et al. |
| 5,900,038 A | 5/1999 | Wilhelm et al. |
| 5,984,994 A | 11/1999 | Hudson |
| 6,017,525 A | 1/2000 | Logan et al. |
| 6,029,395 A | 2/2000 | Morgan |
| 6,029,603 A | 2/2000 | Evans et al. |

* cited by examiner

CONTROLLED RELEASE AGRICULTURAL PRODUCTS AND PROCESSES FOR MAKING SAME

This application claims the benefit of provisional Application No. 60/216,132, filed Jul. 3, 2000 and provisional Application No. 60/254,178, filed Dec. 11, 2000.

BACKGROUND OF THE INVENTION

This invention relates to controlled release agricultural products and processes for making such products. More particularly, the present invention is directed to particulate absorbents in particulate form and holding compositions in particulate form that provide for controlled release of agriculturally beneficial materials such as fertilizers, insecticides, herbicides and fungicides. The particulate absorbents contain capillaries/voids between 10–200 microns in cross-sectional diameter and are impregnated in an amount of 40–95% of the capillaries/voids volume with the agriculturally beneficial material. The process of the present invention forms the controlled release agricultural particulate absorbents by blending the absorbent with the agriculturally beneficial material(s) for a prescribed time. The blended absorbent is fed into a granulator and after screening, the product is dried. The process results in an easily handled, free flowing, controlled release agricultural absorbent based product.

There are many slow and extended release fertilizers with their nutrient release based on time and event related coating failures or coating permeability, and/or low solubility, and/or microbial activity in the soil, and/or a ratio of surface area to nutrient weight of the particle. Of these, the major commercial products are sulfur coated urea, polymer coated ureas, and urea—formaldehyde products such as methylene ureas. The production costs of these materials vary, but all of these commercially available products have been judged by the consumers' spending patterns as too expensive for extensive use in agriculture. This especially occurs in the case of major crops such as wheat and corn which are grown on moist, dry, and irrigated soils under varying weather conditions. In addition, these high priced extended release products are in general not tailored for the short growing periods of wheat and corn because they do not release their nutrients completely within the growing period of these crops. The existing products are tailored for severe water regime nutrient applications, such as rice, sugar cane, and pineapples and high-end truck farm crops, such as strawberries, and cranberries, or shrubs, ornamentals, and flowers. When used for grasses, existing products are limited because of their high cost for use on lawns, gardens, parks, golf courses and commercial, governmental, and educational grounds. The existing products are not extensively used for pasture lands because of the added processing cost of the fertilizer. Furthermore, when existing controlled release products are used for lawn care applications, many purchasers-users primarily desire burn protection caused by overdosing the lawn while applying the fertilizer. They do not necessarily desire long term release properties that the fertilizer may provide.

Thus, a low cost alternative fertilizer with a much shorter controlled release period would be superior to the higher cost, longer controlled/extended release fertilizers.

BRIEF SUMMARY OF THE INVENTION

The present invention includes numerous embodiments of a controlled release agricultural absorbent based product. The absorbent based product includes particles of an absorbent material containing capillaries/voids between 10–200 microns in cross-sectional diameter which is impregnated in an amount of 40–95% of the capillaries/voids volume with an agriculturally beneficial material selected from the group consisting of fertilizers, insecticides, herbicides and fungicides. The absorbent material includes for example, expanded perlite, shredded newspaper, saw dusts, cotton lint, ground corn cobs, corn cob flower, Metrecz absorbent and diatomaceous earth.

The fertilizer includes nitrogen compounds, phosphorous compounds and potassium compounds. The nitrogen compounds include urea, ammonia, ammonium nitrate, ammonium sulfate, calcium nitrate, diammonium phosphate, monoammonium phosphate, potassium nitrate and sodium nitrate. The phosphorous compounds include diammonium phosphate, monoammonium phosphate, monopotassium phosphate, dipotassium phosphate, tetrapotassium pyrophosphate, and potassium metaphosphate. The potassium compound includes potassium chloride, potassium nitrate, potassium sulfate, monopotassium phosphate, dipotassium phosphate, tetrapotassium pyrophosphate, and potassium metaphosphate.

The agriculturally beneficial material also includes micronutrients, secondary nutrients, growth regulators, nitrification regulators, as well as the aforementioned insecticides, herbicides and fungicides.

The particles of absorbent may be agglomerated into granules of a predetermined size.

An important embodiment of the invention is the impregnation of the particle absorbent with a mixture of an interspatial blocker and the agriculturally beneficial material. The interspatial blocker includes plant starches, protein gels, glues, gumming compositions, crystallizing compounds, gelling clays, and synthetic gel forming compounds. The presence of the interspatial blocker acts to regulate the release of the agriculturally beneficial material.

Another embodiment of the present invention includes A controlled release, particulate, agricultural product that includes a mixture of a control release holding substance, such as plant starches, protein gels, glues, gumming compositions, crystallizing compounds, gelling clays and synthetic gel forming compounds, and an agriculturally beneficial material including fertilizers, insecticides, herbicides and fungicides.

The present invention also includes embodiments of processes for making the controlled release agricultural absorbent based product. The process includes, for example, the steps of 1) introducing water to particles of absorbent material to result in absorption of water within the absorbent material, 2) heating the absorbent particles and water to transform the water within the absorbent particles to steam, 3) introducing the heated absorbent particles to an agriculturally beneficial material in aqueous solution to essentially saturate the absorbent particles with the agriculturally beneficial material, 4) granulating the combination of agriculturally beneficial material and saturated absorbent particles to solidify and harden the mixture, resulting in the agglomeration of absorbent particles into granules, and 5) drying the granules.

The present controlled release agricultural absorbent based product and holding material based product provide for fine control of the release over both short and long periods of time, for a variety of agriculturally beneficial materials.

BRIEF DESCRIPTION OF THE DRAWINGS

Further objects and advantages of the present invention will be better understood by carefully reading the following detailed description of the presently preferred exemplary embodiments of this invention in conjunction with the accompanying drawings, of which.

DETAILED DESCRIPTION OF THE INVENTION

Figure 1:
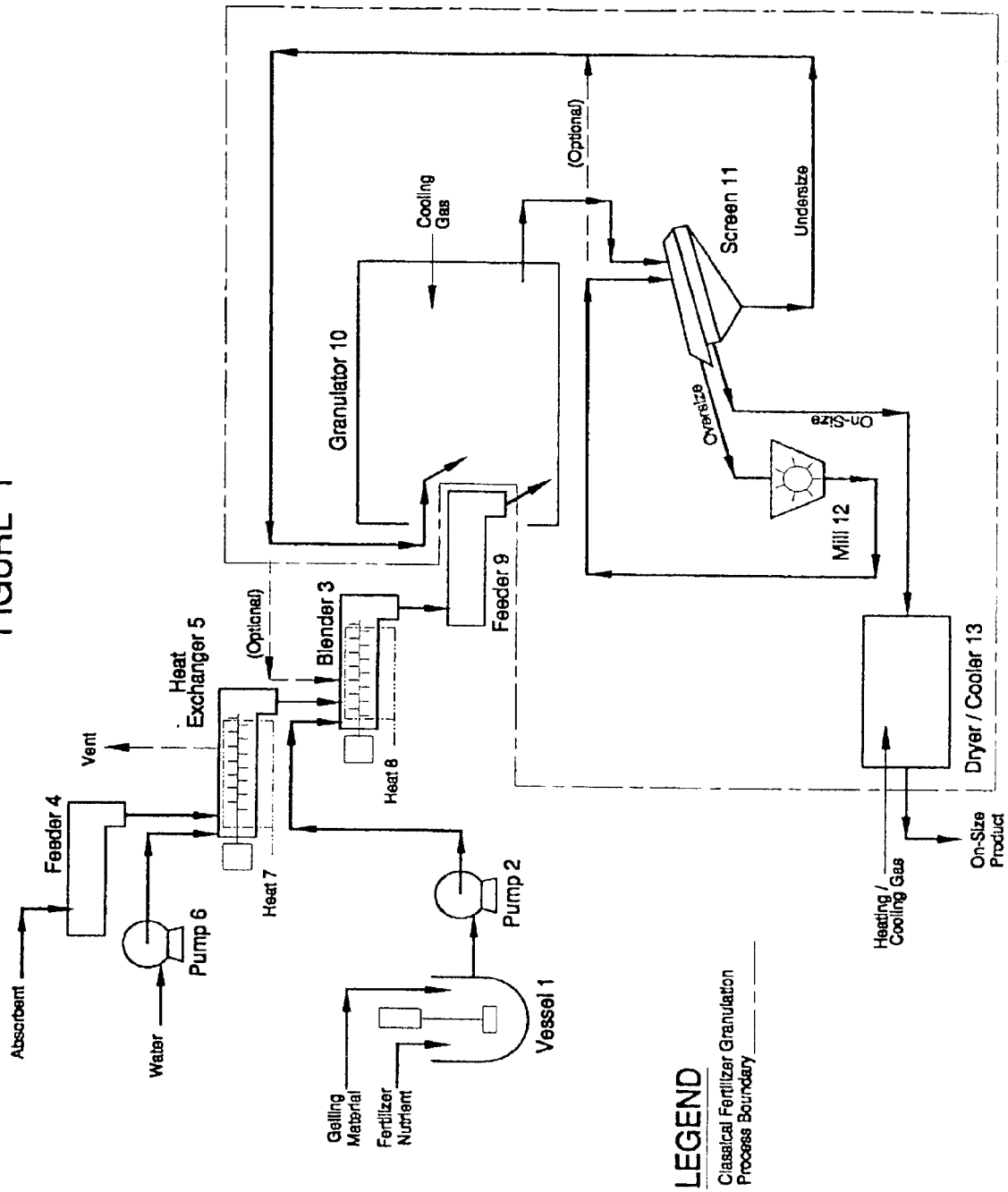
FIG. 1 is a flow chart showing one embodiment of the process of the present invention wherein a controlled release agricultural absorbent based product is produced containing fertilizer and a gel forming interspatial blocker.

One embodiment of the present invention is the newly developed controlled release fertilizer which extends the release of plant nutrient from absorbent particles over a period of time by trapping the plant nutrients in the small capillaries and voids of an absorbing material. Techniques utilize innovative means to provide deep penetration and extensive absorption of an agriculturally beneficial material into the absorbent material. Where this absorbed material contains plant nutrient, the result is a fertilizer with controlled nutrient release characteristics. In most cases, we have been able to further enhance the retention of the nutrient within the absorbent through use of an interspatial blocker such as a gelling compound, which helps further trap the nutrient within the small capillaries and voids of the absorbent material. We have tried many absorbents and methods of absorption, along with several gel forming materials, with varying levels of controlled nutrient release. We have been the most successful where the absorbents are extremely absorbent which results in a relatively dense concentration of nutrient. For testing and development purposes, urea was selected as representative of nutrient/fertilizer agriculturally beneficial materials. It was the nutrient most tested. Best results have been achieved when using perlite as the absorber, although milled newspaper and fine pine sawdust have been very good as absorbents. Utilizing cornstarch as the interspatial blocker (a gelling substance) has improved controlled nutrient release.

Pollution is an ever increasing problem with respect to both air pollution and water pollution. Water pollution occurs when readily soluble fertilizer is solubilized and washed into streams during rains or is solubilized and is leached into the ground water before its intended target vegetation is able to capture. Failure to capture the fertilizer occurs because the target vegetation is not in need of it when it becomes soluble or because the leaching rate is too rapid. Some fertilizers, in particular urea, are lost to the atmosphere through volatilization where urea decomposes to ammonia, carbon dioxide, biuret, and other volatile compounds. Therefore, since the vast majority of fertilizer used has no controlled release properties because they are not available at a low cost, pollution problems are being caused by inefficient use of soluble and volatile fertilizers, which must be applied in excess amounts over the crop's need.

Those who are familiar with the production, storage, transportation, and application of fertilizers know that the nutrient concentration and the physical properties of a fertilizer are extremely important in its acceptance and use by the agricultural community.

Our invention addresses the problems of production, storage, shipping, and application costs, as well as the need for moderation in the length of nutrient availability from slow and controlled release fertilizers. It provides a process that produces a high analysis granular material, for example 40 to 45% by weight nitrogen when using perlite and urea, with or without corn starch, at an extremely low production cost for a controlled release fertilizer. Concurrently, the invention provides a product with physical properties equal to and for the most part more desirable than commercially available urea.

The nutrient strength of commercial urea is commonly recognized as 46-0-0, which is 46% nitrogen. The most common slow release nitrogen, sulfur coated urea, varies from 32% nitrogen to 38% nitrogen depending on its size and the thickness of the coating it is given to obtain the desired release rate. Therefore, substantially more weight (typically 28% more) of sulfur coated urea is required to provide the same amount of nutrient. When this property of a fertilizer is coupled with the physical property commonly called bulk density, which is the amount of weight which occupies a unit of volume, e.g. $lbs/ft^3$, then we have the full impact on the cost of storage and distribution of the fertilizer. In the case of urea and sulfur coated urea, the bulk density is about the same at 45 to 46 $lb/ft^3$.

To achieve a fertilizer which will be accepted by the agricultural community as a replacement for urea and sulfur coated urea, we have developed products which approach the bulk density and exceeds the crushing hardness of urea. Handling characteristics are much better than for sulfur coated urea. Handling and storage do not affect the controlled release properties of our product, but they can, for example, crack the coating of sulfur coated urea. Our product varies in nitrogen strength from 40.0% nitrogen to 45.0% nitrogen, with a more preferred range being 43.0% nitrogen to 44.0% nitrogen. At the same time we had been able to perfect the nutrient absorption and granule forming aspects of the product such that bulk densities have been achieved from 25 $lb/ft^3$ to 43 $lb/ft^3$, with a more preferred range being 35 $lb/ft^3$ to 46 $lb/ft^3$ and the most preferred range being 38 $lb/ft^3$ to 46 $lb/ft^3$. The concentrations of nitrogen using urea and perlite and those bulk densities of final product have been achieved in a laboratory and a pilot plant while maintaining the controlled release properties of the fertilizer. In using larger equipment, as in a full scale plant, with the techniques taught herein, the bulk density is 46 $lb/ft^3$, the same as that of urea and sulfur coated urea while maintaining 44% nitrogen content of the fertilizer and the controlled release aspects of our product.

Several innovative methods were developed to increase the density of the resulting controlled release fertilizer. Such methods provide a superior, concentrated product, having improved handling characteristics and controlled release properties. The product should have a bulk density approaching that of urea to provide economics of storage, transportation and distribution near or equal to those of urea.

In one embodiment of the present invention, our dense, concentrated product is accomplished by the following important features: 1) already expanded perlite is further steam exfoliated beyond its normal popped form to allow better penetration and filling of its interspatial regions by the urea/corn starch mixture; 2) urea/corn starch melts are maintained around 95 to 98% concentration to minimize voids formed from evaporation during the processing; and 3) the small perlite particles containing urea/corn starch are granulated together to form dense, spherical particles.

In general, the process involves taking a proper absorbent material and a fertilizer melt or solution and absorbing the fertilizer melt or solution (which is in a dense saturation state) into the absorbent material and then solidifying the fertilizer within the voids of the absorbent such that it is difficult for the fertilizer to be released by the absorbent when in contact with water or humid conditions. This is done by utilizing a very absorbent material with small capillaries and/or voids and accomplishing the absorbance by keeping the fertilizer and the absorbent above the fertilizer's initial crystallization temperature and at viscosities where capillary action easily occurs while absorption is occurring. For improvements in controlled release characteristics, an interspatial blocker, such as starches and/or other gelling compounds are homogenized into the fertilizer melt or solution before the absorption step of the process. When solidified, these gelling compounds tend to help trap the soluble fertilizer nutrients within the capillaries and/or internal voids of the absorbent. Following absorption and prior to crystallization of the fertilizer melt or solution within the absorbent, the liquid filled absorbent is mixed with recycled material, previously crystallized, to solidify and granulate the liquid filled absorbent with the recycled material through cooling and/or drying, at least partially, imparted by these recycled materials within a pugmill, drum, rotating pan, fluid-bed, or similar standard granulation equipment or combination of standard granulation equipment. Before being stored as product, the granulated solids are milled, screened, further cooled and dried, but not necessarily in that order, by any of the obvious ways before sending the product to storage. The material also is easily prepared using the solids forming techniques which do not use recycle of solid particles for cooling, such as slating, prilling, rotoforming, low pressure extrusion, molding, and forming of bulk slabs or molded shapes. As needed, any of these methods can involve milling of the obtained solids with screening and further cooling and drying as needed with fines recycled to the starting melt or solution filled absorbent for inclusion in the solidification process. The cooling and drying can be accomplished by the use of most all standard methods presently known in the art of granulation including, but not limited to direct gas contact, vacuum enhanced evaporation, and indirect heat exchange.

Although the development can extend to many fertilizer nutrients, we have centered our development work to date on providing controlled release urea. Other nutrient fertilizers which can be used to provide controlled release fertilizer include, but are not limited to the following; ammonia, ammonium nitrate, ammonium sulfate, calcium nitrate, diammonium phosphate, monoammonium phosphate, potassium chloride, potassium nitrate, potassium sulfate, potassium phosphates, such as monopotassium phosphate, dipotassium phosphate, tetrapotassium pyrophosphate, and potassium metaphosphate, and sodium nitrate and combinations of these materials. The urea melt is maintained between 40% and +99.9% by weight urea; however, a preferred range of the melt would be between 65% and +99.9% and a most preferred range between 75% and +99.9% by weight urea. To provide other controlled release fertilizer, one or more other nutrient materials other than urea can be absorbed as long as the nutrients are in the fluid phase by being pure melt or by being solubilized in water or in the melt of another nutrient or combination of nutrients and/or water. For example, a full NPK fertilizer can be made by using urea, monoammonium phosphate, diammonium phosphates, and potassium chloride in various proportions and concentrations, and then blending the product with a filler to provide, for example, 29-3-4, 16-4-8, 10-10-10, 15-5-10, 15-0-15, 22-3-14, 20-28-5, and 12-6-6 control release fertilizers. Further, the nutrients can be in the fluid phase by being in a volatile substance such as e.g. ethanol or methanol as the solvent, which can be evaporated out as the material is solidified and dried. In the above manner, it is possible to prepare controlled release fertilizers containing various mixtures of nitrogen, phosphorus, and potassium as well as incorporation of various secondary nutrients (e.g. sulfur, calcium, and magnesium) and micronutrients (e.g. boron, copper, iron, manganese, molybdenum, zinc) if not all of the secondary and micronutrients, and secondary and micronutrients as well as growth regulators such as, but not limited to, potassium azide, 2 amino-4-chloro-6-methyl pyrimidine, N-(3,5-dichlorophenyl)succinimide, 3-amino-1,2,4 triazole and nitrification regulators such as, but not limited to, 2-chloro-6-(trichloromethyl)pyridine, sulfathiazole, dicyandiamide, thiourea, and guanylthiourea.

The controlled release absorbent particles are small and must be granulated for most commercial application. It is possible to granulate the filled absorbent particles either in their liquid filled or solidified condition with other non-absorbed materials to give controlled release properties to only that portion of the material contained in the absorbent.

See FIG. 1 for a flow diagram of one embodiment of the processes of our invention. The blending of cornstarch and urea, if needed, is done through the use of high shear agitation provided by a homogenizer. The cornstarch addition in tests carried out in the laboratory and pilot plant has worked well. Cornstarch addition can range from 0.01 to 20% by weight cornstarch, with the preferred range being from 0.2 to 10% by weight cornstarch and the most preferred range being from 0.5 to 4% by weight cornstarch. The homogenized mixture is mixed (poured not sprayed) gently with the exfoliated and/or expanded perlite at near the full absorbing capability of the perlite, which is approximately 4 to 7.5% for our exfoliated perlite, by weight of the final product; thus the absorbed urea and cornstarch makes up approximately 95% of the weight of the final product. Prior to the mixing, the exfoliated and/or expanded perlite is preheated significantly above the melt temperature to prevent premature freezing of the melt before full penetration into the perlite. Preheating expanded perlite to temperatures as high as 330° F. has been successful. Preheating of the perlite is desirable but we have made a good product just by keeping the mixture of perlite and melt above the melting point of the urea melt or solution while absorption is occurring. Although full absorption of the urea and fertilizer into the exfoliated perlite or other absorbent is the preferred manner for most products, a reduction in the absorbance will provide a material with less release extension and can be desirable for some fertilizers.

We have been successful by 1) submerging preheated exfoliated and/or expanded perlite in an excessive amount of homogeneous urea/corn starch melt or urea melt, and then extracting the fully absorbed particle from the homogeneous melt for granulation; 2) pouring the homogeneous urea/cornstarch melt or urea melt into the preheated exfoliated and/or expanded perlite with gentle mixing until the absorbing capacity of the perlite is obtained before granulation; or 3) in mixing simultaneously metered amounts of exfoliated and/or expanded perlite and urea/cornstarch melt or urea melt and blending them together with gentle mixing while maintaining the melt and perlite above the solidification point of the melt before granulation. Then for all three methods of blending, the resulting blended material is added directly to a pan/drum granulator or pugmill, with recycle and allowed to agglomerate and solidify into granules or is premixed with or without recycle before adding it to the pan/drum. The resulting granules are screened and the oversize is milled and recycled to the screen. The undersize is recycled back to the granulator where it is agglomerated with the incoming mixed material. In another option, we have been successful in returning the oversize directly to the perlite urea/corn starch mixing step, Vessel 2. Steam can be used to enhance granulation, but our laboratory tests have not shown this is required. The product granules are quickly and easily dried in a pilot plant or laboratory fluid-bed operating with approximately 190° F. entering air. The dried granules are then cooled and conditioned against caking, if necessary, before going to storage.

All of the exfoliated and/or expanded perlites we have used have worked well. The inside microstructure of an exfoliated and/or expanded perlite particle is comparable to a honeycomb type arrangement; the individual cells indicate diameters of 10 to 200 micron, with a preferred range being 25 to 150 microns, and the most preferred range being 40 to 100 microns. As such, the exfoliated and/or expanded perlite used can have a loose weight density of from 2 to 20 lb/ft$^3$ with a preferred range of 2 to 10 lb/ft$^3$ and a most preferred range of 2 to 6 lb/ft$^3$.

One skilled in the art readily will see that the agglomeration and otherwise granule forming, drying, milling, and screening portions of the process are similar to that of a pan/drum agglomeration type granulation process and that of a fluid-bed or prilling granulation process and as such the innovative portion of our process can be easily incorporated into existing and idle fertilizer granulation plants. See the dashed line enclosure of FIG. 1 for the existing plant equipment. Tests have shown that drying can be performed at lower temperatures and without the use of fluid-beds, e.g. within a standard rotary drying drum. The milling step which is obviously forbidden in coated products appears to have no significant adverse effect on the controlled release characteristics of this new invention when milling uses a knife bladed hammer mill similar to those used in large urea granulation plants.

For the most economical process, it is preferred to have the urea as a melt of concentration around 78 to 85%. The urea can be taken directly from the urea synthesis plant and does not need to pass through an evaporator, concentrator per the normal route toward granulation or prilling, hence biuret formation which occurs in the normal granulation urea process of melt concentration and then granulation at high temperatures is avoided. Further, the added costs for production of a controlled release urea fertilizer over that of just urea granules is only the cost of the perlite and, if used, the cornstarch or other gelling additive, and the cost of mixing them with the urea. However for more dense products with enhanced controlled nutrient release characteristics, and the use of less absorbent, we teach the use of higher concentration melts up to 99.9% melt.

The products made by our invention continue to retain excellent handling characteristics with regard to hardness and abrasion resistance and can be made in all size ranges desired by the lawn and garden users as well as the agricultural users. In some cases, by using 78% to 85% by weight urea melt, we can achieve better penetration of the cornstarch within the capillaries and voids of the absorbent material than with +99.9% melt. This increased penetration is apparently due to several reasons; among them lower viscosity of the homogeneous mixture, almost no foaming of the mixture with cornstarch during processing, and reduced pre-gelling of the cornstarch prior to entrance into the exfoliated and/or expanded perlite. When the absorption is done without cornstarch or any additive absorbed into the perlite using the same methods as with cornstarch, significant reductions in controlled release characteristics occur.

All absorbents will not work; it now appears that only those with capillaries and voids between 10 and 200 microns in cell diameter can be used. Further it appears that others, which may work from a controlled release standpoint, have much too small an absorbing capacity, greatly diluting the nutrient content of the fertilizer particle and thus increasing the cost.

In our work to date we have made granular-product of a size from 1 mm to 4 mm; however, we have made granules ranging in size from 0.20 mm to 25 mm. These larger and smaller granules have control release properties and product of this size can be made with only a change in the process screen size. It is preferable to have granules of about 0.20 mm when producing a product to be used on golf greens. The 25 mm product would be used in rice patties. The most useful range for lawns and most agriculture is 1 mm to 4 mm granules. Material with a size of 6 mm to 8 mm will be useful for forestry fertilization.

The urea used can contain normal conditioning additives like formaldehyde, previously reacted urea formaldehyde, clays, ligno products, or parting agents. The presently produced product has shown some excellent handling characteristics. Unlike some controlled release products, it has little tendency to float and it can be blended with most other fertilizers or used directly without blending.

We have successfully made a product using urea melt concentrations up to +99.9% urea melt without cornstarch addition, but at a loss of some controlled release characteristics and some good physical properties because of the absence of the corn starch. Further processing at above about 98% urea concentration leads to excessive formation of biuret, a compound which is undesirable to many agricultural users because of its toxic properties with some crops, in particular, citrus crops. This requires preheating and/or keeping the absorbent above the solidification point of the urea melt and preferably about 20 to 30° F. above that point.

In our work along with the granulation process techniques otherwise mentioned, we have experienced success in making the controlled release absorbent based product when using a compaction step, by making a homogenous mixture of cornstarch and urea, or using just urea and then mixing the mixture with the perlite or other absorbents, i.e. shredded newspaper, various saw dusts, cotton lint, ground corn cobs, corn cob flower, Metrecz absorbent, diatomaceous earth, and others. Then we solidify the material by pouring it out on a flat metal sheet to cool. Following this, the product is milled to the desired particle size; however, when employing a compaction step it is typically milled and compacted into the desired particle size. The controlled release characteristics of the product are usually reduced by the compaction step.

Many other pure nutrients and combination of nutrients can be made utilizing the process techniques taught by our disclosure.

In further embodiments of this invention, insecticides such as 0,0-diethyl O-(2-isopropyl-6 methyl-4 pyrimidinyl) phosphorothioate), herbicides such as 2,4-dichlorophenoxyacetic acid, fungicides such as ferric-dimethyl-dithiocarbamate, growth regulators such as gibberellic acid, and other agricultural chemicals such as methiocarb can be added during the absorption phase of this process to obtain controlled release characteristics to a complete set of a crop's chemical and nutrient needs. Table 1 includes some more of these chemicals, but those that can be added to the product during the absorption phase are not limited by this list.

Other plant starches, protein gels and glues, gumming products, crystallizing compounds, gelling clays, and synthetic gel forming compounds also work as the gelling and/or inter-spatial blocking compound. These include but are not limited to the following: rice starch, potato starch, wheat starch, tapioca starch, and any starch which contains the D-glucopyranose polymers, amylose and amylopectin; modified starch of the former listing (also including corn starch) by acetylation, chlorination, acid hydrolysis, or enzymatic action which yield starch acetates, esters, and ethers; starch phosphate, an ester made from the reaction of a mixture of orthophosphate salts (sodium dihydrogen phosphate and disodium hydrogen phosphate) with any of the listed (also including corn starch) starch/or starches; gelatin as made by hydrolysis of collagen by treating raw materials with acid or alkali; glue as made from any of the following: collagen, casein, blood, and vegetable protein such as that of soybeans; gumming products such as cellulosics, rubber latex, gums, terpene resins, mucilages, asphalts, pitches, hydrocarbon resins; crystallizing compounds such as sodium silicate, phosphate cements, calcium-oxide cements, hydraulic cements (mortar, gypsum); gelling clays in the form of very fine powders; synthetic gel forming compounds such as polysulfide sealants, polyethylene, isobutylene, polyamides, polyvinyl acetate, epoxy, phenolformaldehyde, urea formaldehyde, polyvinyl butyral, cyanoacrylates, and silicone cements. Plant starches work particularly well, especially corn and wheat starches.

All granules made can be rounded and/or coated, if desired, with hydrophobic materials such as waxes, polymers, or oils to further enhance their controlled release characteristics.

Scanning electron photo micrographs of our expanded perlite showed the expanded perlite to be an in-depth formation of small micro sized chambers connected by walls which are about 0.5 micron thick which formed when water evenly dispersed in the unexpanded perlite expanded under high temperature. For the most part, the expansion of the perlite particles, which are sized before expansion by milling the larger mineral rock, result in particles which appear to have outer shells with blow-holes in the shells. This original perlite expansion can be done by any one of several known technologies. We find that though the resulting expanded perlite has potential, it does not allow us to produce the dense product we desire. Therefore, we subject the expanded perlite to further treatment in our pilot plant. A small quantity of water is applied to the expanded perlite, our most preferred amount being from 0.5 ml of water/gm of perlite to 5.0 ml of water/gm of perlite. The treated expanded perlite is then introduced into a heated chamber, most preferably a steam jacketed double shaft pugmill running at a high rate of speed so as to mechanically fluidize the particles. This heats the wetted expanded perlite up again such that the water in the perlite expands within the perlite but this time in a much more gentle fashion than the original high temperature and pressure popping technique used in the original expansion. Air temperatures within the vessel can range from 210° F. to 500° F. with the most desired range being 215° F. to 350° F. The result as shown by the electron microscope is increased rupture and exfoliation of the outer shell as the absorbed water expands into steam at atmospheric pressure. There appears to be less effect on the vast maze of internal chambers. The retention time that the wetted perlite spends in the expansion chamber (or pugmill) needs only to be about 30 seconds, but extensive exposure of over an hour is not detrimental unless the mechanical action is too violent and abrades the perlite. The perlite with this enhancement to the original expansion is now ready to be filled with our urea/corn starch mixture. This step of controlled exfoliation of the perlite with steam immediately before it is introduced to the absorbing vessel also drives most of the air from the internals of the previously expanded perlite replacing it with steam. Since urea and urea solutions are extremely hydrophilic as are most fertilizers, the steam in the perlite is absorbed by the fertilizer mixture causing a psuedo vacuum within the perlite which further assists complete filling of the perlite with urea/corn starch solution or melt when the perlite is fully immersed in the molten material. We have achieved the same exfoliated results in the laboratory using a small tank fitted with a condenser, in a pressure cooker and with a microwave oven. In each case, to get a further rupture of the outer skin of the expanded perlite, water had to be applied to the expanded perlite prior to heating. Scanning electron photo micrographs and calculations, based on percentage of components in the final product and bulk density in the final product, indicate that in the final product, the exfoliated perlite is impregnated to between 40 and 95% of its holding capacity and in most cases, impregnation is between 60 and 90% of its holding capacity. In the most preferred cases, impregnation is between 80 and 90% of the capillaries/void volume. Thereby, the impregnated mixture makes up 70 to 95% by weight of the final product. About 60 to 80% of the urea/corn starch mixture is absorbed into the exfoliated perlite. The remaining urea and corn starch acts as a binder holding the individual granules together and that urea is available for quick release to the soil.

Another major contributor to the high bulk density is the fact that we can granulate the material in the same manner as urea is presently granulated. This is accomplished by spraying the mixture consisting of molten urea, corn starch, and the small perlite particles containing absorbed urea/corn starch mixture, and which vary in size from about 100 micron to 1500 micron in diameter, but more preferably 150 to 1000 microns, onto existing recycle granules in a rotating drum. The existing granules thus grow in size because of the onion skin type build-up from direct solidification of the mixture sprayed on them and because there is some agglomeration of small existing granules in the rotating bed being adhered to large granules by the solidifying mixture which acts as an adhesive. By such a manner the granules are made spherical. They are then sized as they leave the granulator as per a typical urea granulation plant, with the undersize being returned to the granulator and the oversize being milled and returned to the granulator either in total or just the undersize part after rescreening. The resulting product is spherical even though each granule is made up of a multiplicity of perlite particles filled with solidified urea and starch and the unabsorbed urea and starch acting as the adhesive to hold the granule together. Later when the granules are applied to the soil and water begins to leach-out the urea nutrient, the corn starch not only acts as a inter-spatial blocker thus retarding the leaching of the urea it helps hold the perlite particles together which also enhances controlled release of the nutrient by, in effect, maintaining a larger center of high nutrient content, rather than allowing the dispersion of the small perlite particles in the soil. Also, in effect, maintaining a large urea granule which obviously goes into solution slower than the same granule ground to a powder and dispersed in the soil.

Our granules are extremely hard when made at high density even without the customary inclusion of 0.3% to 0.5% urea formaldehyde in urea granules to harden them up and prevent caking. The exfoliated perlite super-structure apparently gives extra hardness (crushing strength) to the granules such that the crushing strength of −6+7 Tyler mesh, (3.4 mm to 2.8 mm in diameter) materials vary from 8 lbs of force to 10 lbs of force without the addition of urea formaldehyde as a hardening and conditioning agent. This is due to using concentrated urea of 95%, and spray agglomeration granulation. In comparison, typical commercial urea with 0.3% to 0.5% urea formaldehyde at −6+7 Tyler mesh (3.4 mm to 2.8 mm in diameter) has a hardness (crushing strength) of 5 to 8 lbs of force, but without formaldehyde, are much weaker.

Urea hardness (crushing strength) varies directly in a straight line manner with granule diameter, with a curve of the type $y=mx+c$, where $y$=the hardness, $x$=the diameter of the granule, $m$=the slope of the curve, and $c$=the intercept of the x-axis. Using this curve equation with the normal intercept as determined by classical data at 0.75, we can predict the hardness (crushing strength) of our urea/corn starch product to range 11 to 14 lb of force when the granules are 4 mm in diameter and 0.9 to 1.1 lb of force when the granules are 1 mm in diameter.

With regard to the use of urea formaldehyde as the recognized manner of preventing urea caking during storage and shipment, we have used some urea pretreated with 0.4% urea formaldehyde in our tests to determine any positive or adverse effect its presence might have on the controlled release characteristics of our material. Some may wish to re-granulate urea by melting or dissolving standard commercial product or they may wish to add urea formaldehyde to resist caking or other reasons. To demonstrate this was possible we did some limited testing. In our test work, we were able to make a product with some increased extension to the release rate.

To measure the relative solubilities of the products in soil, an irrigated soil burial test was devised such that granules could be retrieved for measurement of their nitrogen content. The following is a description of the test.

Procedure for Controlled Release Soil Test
1. Screen the sample to obtain −6+7 Tyler mesh granules for the test.
2. Label a freezer container with the test description.
3. Place the freezer container on the 1200 g balance and tare out.
4. Place 300 g of potting soil with a 40% moisture content into the container and record the weight.
5. Over the soil place two (2) pieces of fiberglass mesh with 14 meshes to the inch and 1/16 inch openings.
6. Tare out the container with the soil and fiberglass mesh screens.
7. Spread 5 grams of −6+7 Tyler mesh granules over the screen in a single layer and record the weight.
8. Place a large square of fiberglass mesh over the granules, with a stainless steel screen cut to fit over it, so that the shape of the container has been mirrored.
9. Once this is shaped, tare out the container and add 150 g of soil and record the weight.
10. Repeat this process for each sample to be tested (in triplet if possible).
11. After all containers are completed, fill a mist spray bottle with de-ionized water and prime.
12. Tare out the weight of the primed mist bottle.
13. Mist 4 g of water into each container and immediately place the lid on container and seal.
14. After the fertilizer granules have been submerged in a humid soil environment for the allotted time (9 hours, 24 hours, and 3 days), the 150 g of soil is removed from the container.
15. Weigh to the nearest 0.0001 g in aluminum weigh pan and tare out.
16. Gently remove the two pieces of fiberglass mesh, which contains the remaining fertilizer granules.
17. Transfer the granules to the aluminum weigh pan and record the weight of the fertilizer granules.
18. Place the fertilizer granules in a laboratory oven to dry at low temperature (50° C.) for 13 hours.
19. Remove the dry sample from the oven, weigh to the nearest 0.0001 g and record weight.
20. Place the dry fertilizer sample into a 125 mL plastic sample bottle containing 20 g of de-ionized water.
21. Allow the sample to dissolve for 3 hours.
22. Place approximately 1 ml aliquot of the sample solution onto the sample stage of a refractometer (e.g., Abbe Refractometer).
23. Record the refractive index and temperature of the solution.
24. Calculate the percent urea retained from the original fertilizer sample.

Using the above procedure, plain urea particles went into solution in the first 9 hours. Perlite granules containing urea and 1% corn starch and made from 85% urea melt retained up to 42% of their nutrient after 9 hours, 23% after 24 hours, and 11% after 3 days, thus providing an extended control release pattern. Further extended control release of the granules resulted when 1% cornstarch was used as a gelling compound with a 95% urea melt; up to 48% of the nutrient remained in the perlite after 9 hours, 23% remained after 24 hours, and 11% remained in the perlite after 3 days.

This is much less controlled retention than the goal of most sulfur coated ureas and methylene ureas, which are relatively expensive, longer nutrient availability extending materials.

Alternatively, cornstarch and cold water (33° F.–43° F.) can be blended at ratios of as little as 1 to 1 (i.e. cornstarch is equal to or less than 50%) and then mixed with the urea melt before the absorption step of the process and thus avoid the homogenizer step in the process. This, however, adds water to the melt which must be dried out of the product, and for a continuous plant process would not be desirable.

While urea was employed in the tests as the principle source of nitrogen, diammonium phosphate (DAP) was additionally used as a source of nitrogen, as well as a source of phosphorus.

The control release fertilizer of the present invention was applied to outdoor plots of grass as described in Example 16. Two sample embodiments of the present controlled release fertilizer were prepared using urea, corn starch and expanded perlite. One sample fertilizer was prepared using a 1% corn starch solution and the second sample fertilizer was prepared using a 4% corn starch solution. An 85% urea solution was employed in preparing both the 1% and 4% sample fertilizers. Test results show that the controlled release fertilizers provided the shortest time from planting to tasseling and silking for both sweet corn and field corn.

TABLE 1

CHEMICAL NAME 2-(2-Methyl-4-chlorophenoxy)propionic acid
2-Methyl-4-chlorophenoxyacetic acid
3,6-Dichloro-o-anisic acid
Pyrethrins
2-chloro-4-ethylamino-s-triazine
Benefin: N-butyl-N-ethyl-alpha, alpha, alpha, trifluoro-2,6-dinitro-p-toluidine
Trifluralin: alpha, alpha, alpha, trifluoro-2, trifluoro-2,6-dinitro-N,N-dipropyl-p-toluidine
Dithiopyr 3,5-pyridenedicarbothiocic acid, 2-(difluoromethyl)-4-(2-methylpropyl)-6-(trifluoromethyl)-S,S-dimethyl ester
Chlorpyrifos[O,O-diethyl-O-(3,5,6-trichloro-2-pyridyl)phosphorothioate
O,O-Diethyl S-(2-(ethylthio)ethyl)phosphorodithioate
(2,2,2-trichloro-1-hydroethyl)phosphonate
1-((6-chloro-3-pyridinyl)methyl)-N-nitro-2-imidazolidinimine
Cyano(4-fluoro-3-phenoxyphenyl)methyl 3-(2,2-dichloroethenyl)-2,2-dimethylcyclopropane carboxylate
(2,4,6,8-tetramethyl-1,3,5,7-tetraoxycyclo-octane)
Prodiamine, (N3, N3-di-n-propyl-2,4-nitro-6(trifluoromethyl)-m-phenylenediamine)

More specifically, our invention encompasses taking urea melt of concentrations 40% to 99.9%, or more preferably 65% to 99.9%, and most preferably 75% to 99.9% made by any means and corn starch made by a means and blending them together into a completely homogeneous mixture and in such a way that the gelling properties of the corn starch are not destroyed and foam formation is minimized. We blend under atmospheric pressure and do not let the temperature of the mixture exceed 295° F. or a point where the vapor pressure of the mixture exceeds 450 mm of Hg while maintaining the temperature of the mixture above the point of first crystallization for urea. More preferably, we do not exceed 280° F. or a point where the vapor pressure of the mixture exceeds 350 mm of Hg and most preferably we do not exceed 270° F. or a point where the vapor pressure exceeds 300 mm of Hg. This prevents foaming which hinders the later absorption step, limits formation of biuret, and limits thermal damage to the corn starch.

We minimize the mixing step and use only enough homogenization to completely mix the corn starch within the urea solution. We use urea solution with more than 40% urea content up to 99.9% urea; however, to provide a more dense product and to get better extension of the release, we more prefer to use urea solution with a urea content between 65% and 99.9% and most prefer a urea solution between 75% urea and 99.5% urea. Further, we keep the melt at least 0.5° F. above the point of first crystallization for the urea/corn starch mixture; however, we prefer to keep it at least above 2° F., and most prefer to keep it at least 5° F. above the point of first crystallization. Once the mixture has been made, it is important to quickly absorb it to prevent damage to the corn starch gel and to prevent excessive biuret formation. We pump and meter the mixture without temperature adjustment into a pugmill where it is mixed with the absorbing exfoliated perlite. Although others who utilize our technology may wish to adjust the temperature, we find temperatures adjusted at this point can cause foaming or crystallization which at this point are very harmful in obtaining maximum absorption into the expanded perlite. Expanded perlite by any of most standard means is heated to above the point of first crystallization of the mixture to avoid premature freezing of the mixture in the outer chambers of the perlite and thus prevent full penetration. The metered perlite can be heated by a fluid-bed or any number of ways and passed to the absorber, however, we prefer to provide a secondary step of limited exfoliation to the perlite as follows for much better absorption and controlled release. A mixture of perlite and water may be heated to steam the perlite, or hot steam may be introduced directly to the perlite to steam the perlite.

The preferably hot steam filled perlite is fed to the absorber where it absorbs the mixture to near completeness. More urea/corn starch mixture is used than the absorbing capacity of the perlite so that the perlite is essentially totally submerged in the urea/corn starch mixture. This allows the excellent penetration and fill of the perlite particles. To give the mixture time to completely penetrate into the perlite before being crystallized or gel setting the absorbers side walls are heated at the same temperature as the perlite-slurry and the top is covered to prevent evaporation. Although we do this in continuous fashion in a pugmill, it is obvious to those schooled in the art that some other absorber vessels may work just as well or to a limited degree as long as early crystallization of the mixture is not allowed. There must be excess in urea/corn starch over that which absorbs for this mixture is used as the mortar which covers and joins the individual pieces of perlite, now partially or totally filled with the urea/corn starch mixture, together into granules made up of a multiplicity of these filled perlite particles. Retention time in the absorber can be from 10 seconds to several hours, however, we prefer to provide the time to obtain maximum penetration and yet minimize the time with respect to avoiding excess formation of biuret and damage to the corn starch gel. Thus we more prefer 30 seconds to 30 minutes within the absorber, and most prefer 1 minute to 15 minutes within the absorber.

Once the urea/corn starch mixture is absorbed into the exfoliated perlite to the extend desired, the mixture is still a slurry of urea/corn starch containing perlite in a mixture of urea and corn starch, as such it is pumped by mechanical, pressure or suction means into the granulator. We have found that a course dispersion spray such as is used in most commercial drum granulators is preferred although we have been successful in pouring the material into the rolling bed of granules and in pressure spraying the material with steam. When doing this, recycle as undersize and milled oversize and product, if needed, is fed back to the drum to provide cooling as needed and to assist in particle formation and agglomeration. Much of the cooling is provided by the evaporation of water from the granules. We have found that the best temperature for granulation is to provide entering recycle at from 110° F. to 220° F., but more preferably between 130° F. and 210° F., and most preferably, between 150° F. and 205° F., with the perlite/corn starch slurry fed into the drum at from 32° F. to 295° F., but more preferably, from 115° F. to 280° F., but most preferably, between 160° F. and 270° F., but not allowing the temperature of the granules in the drum to exceed 235° F. The rolling action and spraying action combine to form hard spherical granules with a good gel structure and with controlled release properties.

Figure 2:
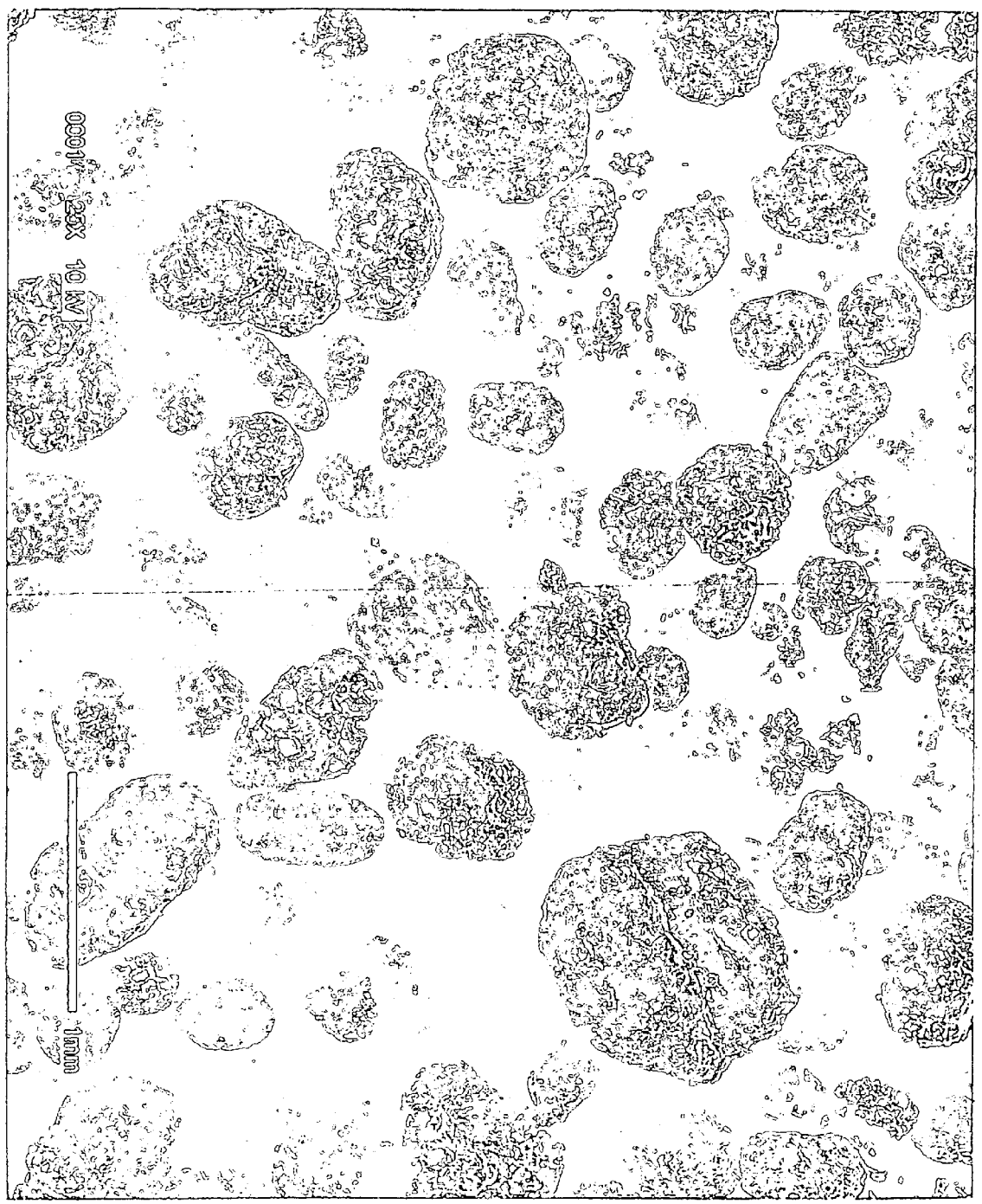
FIG. 2 is a photomicrograph showing expanded perlite wherein the particles appear to be covered with a thin shell.
Figure 3:
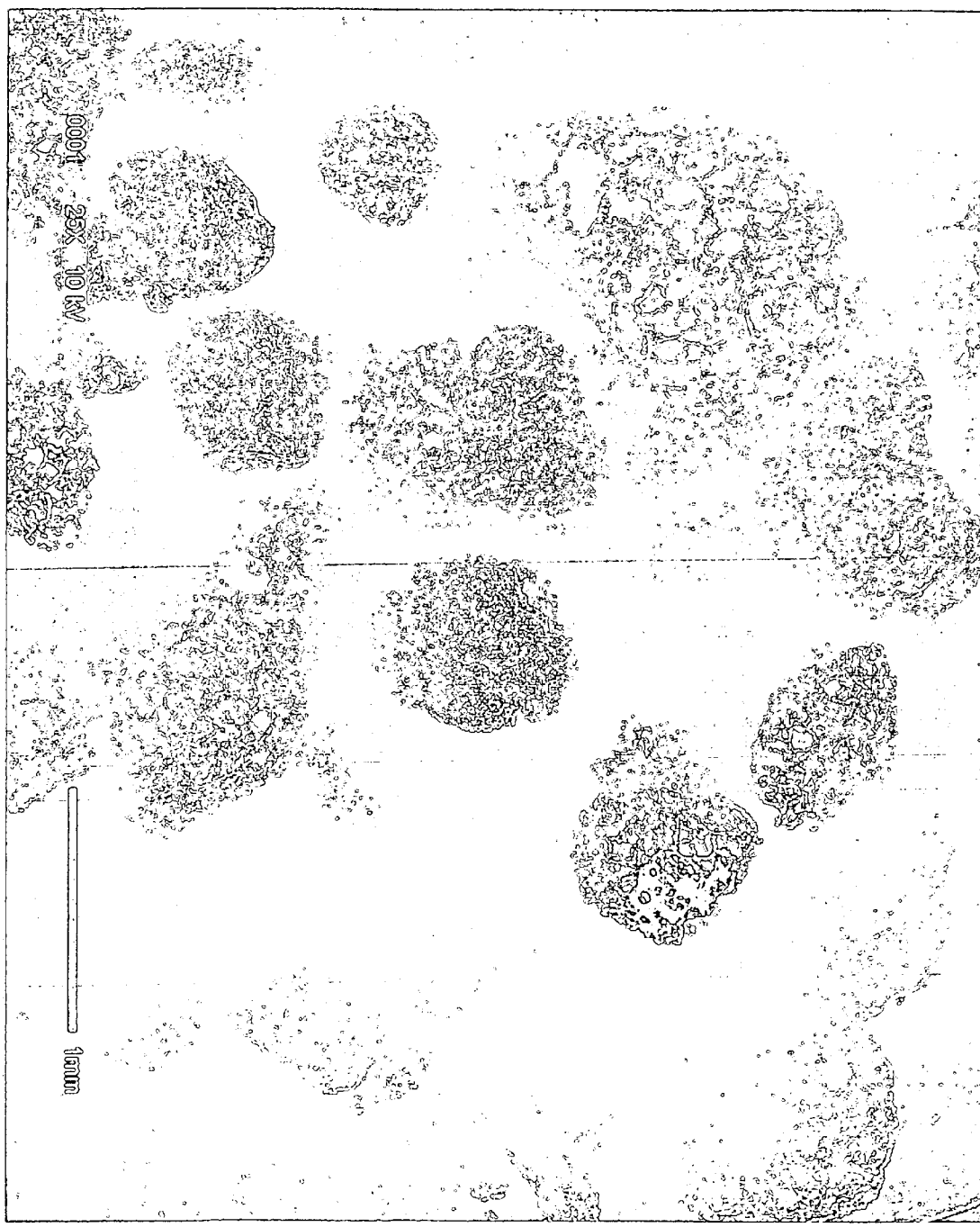
FIG. 3 is a photomicrograph showing exfoliated perlite wherein the internal capillaries and voids are exposed.

The difference between normally expanded perlite and exfoliated perlite as taught by our invention is shown by the following photo micrographs. FIG. 2 shows the expanded perlite to be spherical to oblong in shape with an average size of about 0.5 millimeters=500 microns. Some openings are apparent on some of the material, but most of the particles appear to be covered over with a thin shell. After steam exfoliation within the pugmill of the pilot plant, as shown in FIG. 3, the outer covering is efficiently removed revealing the expanse of the internals. In essence, totally changing the absorbency of the perlite. A close up of an exfoliated granule in FIG. 4 shows just how open the perlite is to penetration by the urea and/or urea/corn starch mixture.

Figure 4:
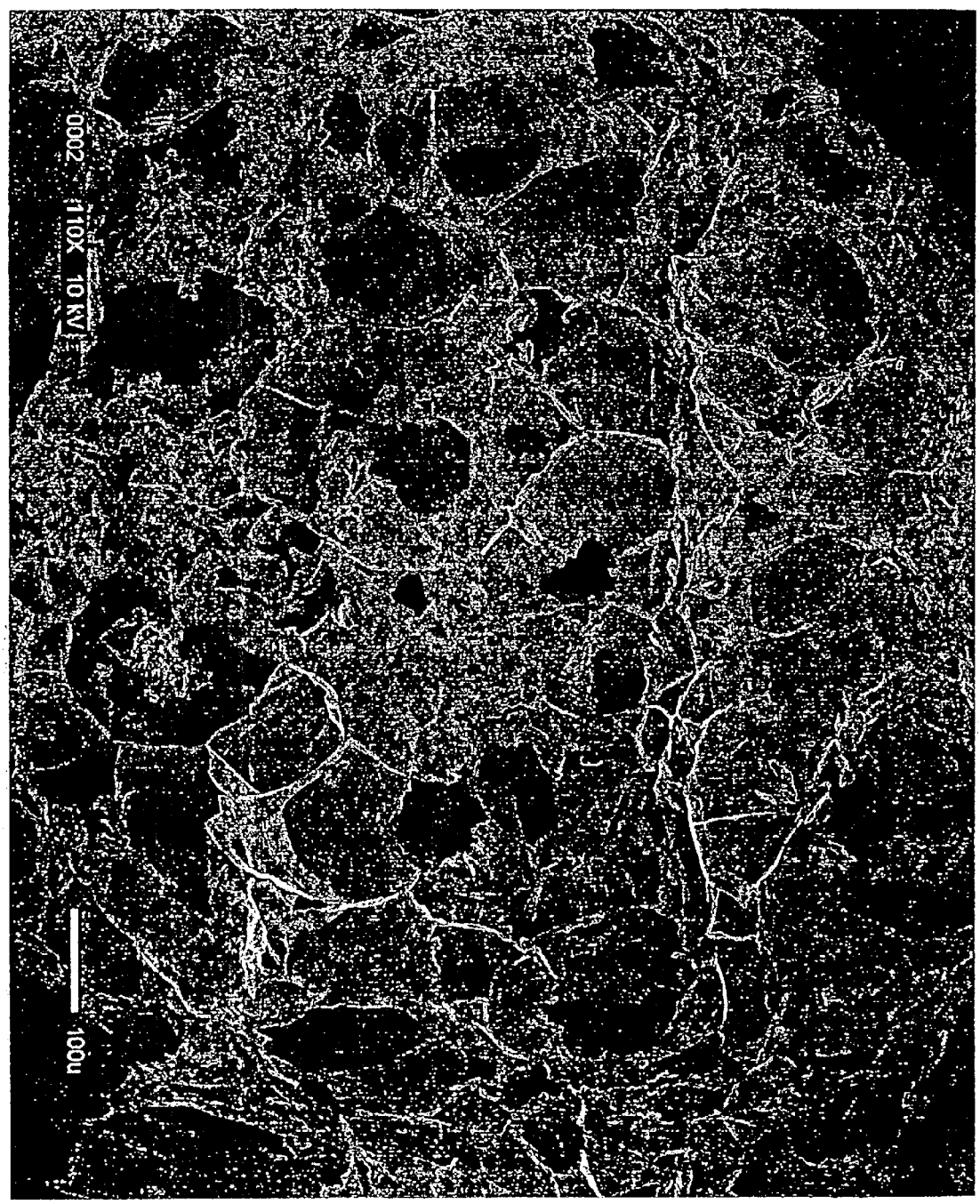
FIG. 4 is a photomicrograph showing the exfoliated perlite of FIG. 3 at higher magnification to observe the greater exposure of internal capillaries and voids.
Figure 5:
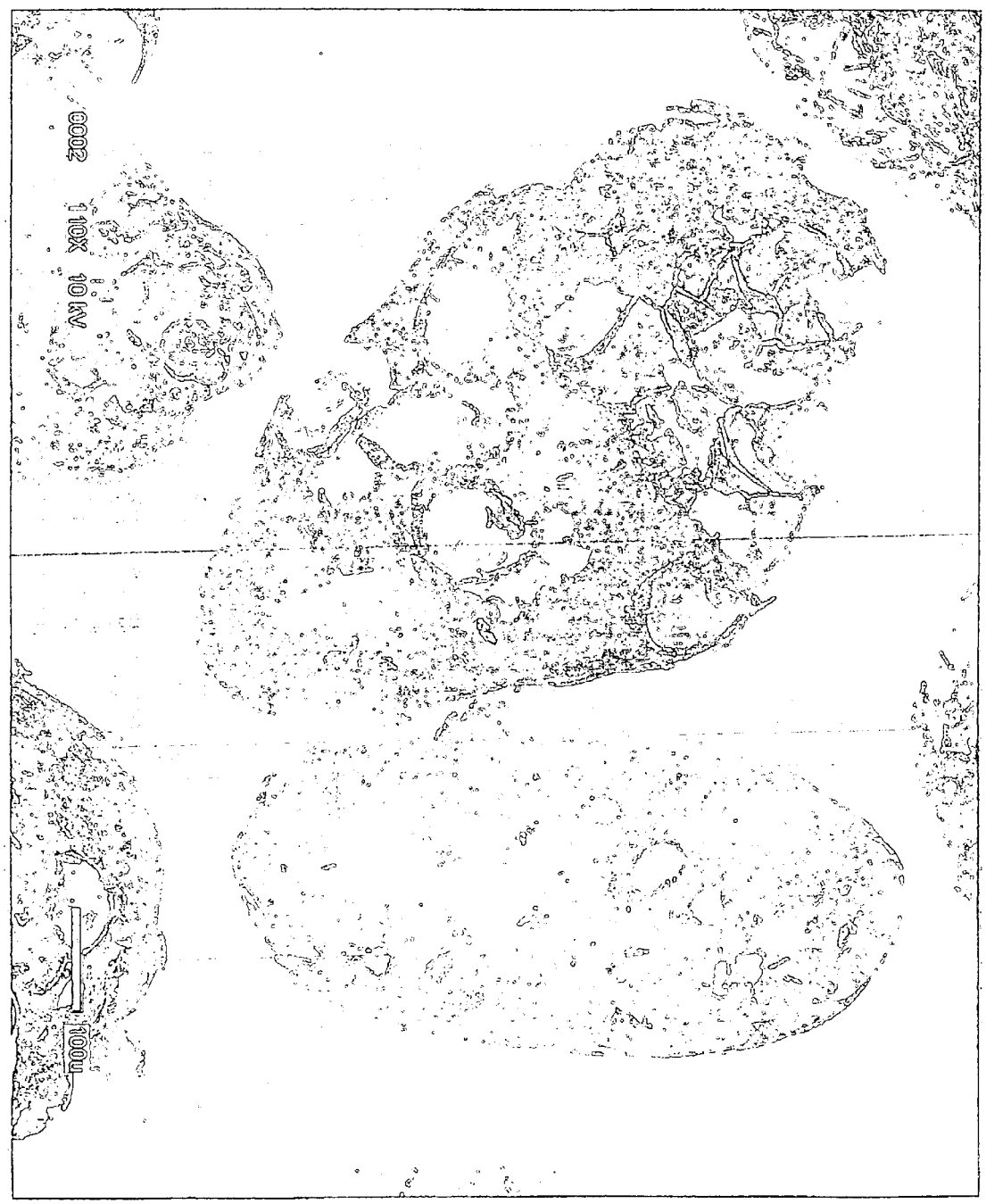
FIG. 5 is a photomicrograph showing the expanded perlite of FIG. 2 at the higher magnification as in FIG. 4 in order to compare the relatively closed surface compared to the exfoliated perlite of FIG. 4.

A close up photo micrograph of expanded perlite, as in FIG. 5, in contrast to FIG. 4, shows limited exposure to the perlite internals to the urea or urea/corn starch mixtures. It also reveals a much easier means of egress by the absorbed mixture when it is in the soil, thus allowing the control and extension of nutrient release by the amount and type of blocking agent mixed with the urea or other nutrient.

With reference to FIG. 1, one embodiment of the process of our invention includes taking fertilizer nutrient as a solution or as a melt and homogenously mixing it with a gelling material, i.e. blocking agent, in vessel (1) containing a high sheer homogenizer. However, if the mixture is, e.g. a starch or similar material, and the solution is relatively cold, a homogenous mixture of the solution and the blocking agent can be obtained with less mixing force.

The homogenous solution is then pumped in a continuous manner by a metering pump (2) to a blender (3) to mix with an absorbent. The absorbent is likewise continuously fed to the blender by being metered by a solids feeder (4) to a blending type heat exchanger (5) to which water is also metered through a pump (6) and added to the absorbent prior to complete heating of the absorbent and in a manner that it is evenly dispersed among and within the particles of the absorbent. Heat (7) is applied indirectly to the absorbent and water in the heat exchanger in a controlled manner to cause the water to expand to steam as the absorbent passes through the heat exchanger, this prepares the absorbent for maximum absorbency when it reaches the blender (3). Heat (8) is applied to the blender to individually heat the contents and maintain good temperature control for optimum absorbency. In the blender the absorbent absorbs the mixture prepared in vessel (1) but not all of it; leaving an essentially filled absorbent with excess of that mixture in a very viscous but flowable condition to be discharged from blender (3) to feeder (9). Thereby it can be introduced into the granulator (10) by a number of means. The filled absorbent particle with the absorbent mixture are granulated within the granulator such that the mixture crystallizes both within the absorbent particles and outside the absorbent particles, the latter thus acting as the glue to hold the individual particles together into the form of a granule containing many particles. The granules discharge from the granulator after the particles and their contents and the accompanying mixture, making up the granules, are solidified by the loss of heat and/or increase concentration. The heat of crystallization is removed by incoming recycle provided by the undersize from a sizing screen (11) and/or cooling gases passing through the granulator and/or heat losses passing through the shell of the granulator and/or by evaporation of water or other solvent from the granules or evaporation cooling from other means within the granulator. In some cases heat will replace cooling to evaporate the solvent, thus increasing concentration of the mixture, both within and outside the absorbent, and resulting in solidification of the mixture. Within the granulator, the particles from feeder (9), not only agglomerate among themselves, they also build on and agglomerate with the incoming recycle of undersize. Discharge from granulator (10) then free flows to screen (11) where the oversize is separated and sent to a mill (12) and then back to the screen (11). As an option to allow the best sphericity product, the milled material is all returned to the granulator. The on-size material leaving screen (11) free flows to a dryer/cooler (13) where it is dried to the desired completeness and cooled to a proper storage temperature. Optionally, portions or all of the undersize and milled oversize can be returned to the blender (3) as is needed to improve granulation.

More specifically, we prefer that the heat exchanger (3) be a moderately high tip speed pugmill with heated sidewalls, and that heat be provided by steam whose pressure at saturation can be easily regulated for a constant temperature control. The heat exchanger (3) should be vented but only to let out the air and steam which would otherwise build to a pressure condition within the heat exchanger. We prefer to maintain as much as possible a steam atmosphere within the pugmill, which is produced by evaporation of the water dispersed into the absorbent, and to discharge the exfoliated and/or steam containing absorbent directly to the blender (3). The blender is preferred to be a pugmill with moderate to slow tip speed, such that the mixing is gentle but thorough. The material should reach a moderate oatmeal consistency as it exits the pugmill blender (3). We prefer the feeder (9) to be a low pressure developing pump or screw conveyor.

In other feeding means, we have been successful with a steam eductor whereby the filled absorbent and excess mixture is sprayed onto the granules in the granulator. The granulation system which consists of the granulator, screen, mill and drying and cooling means and associated supporting equipment can be most any classical commercially existing system including spray drum granulators, pan granulators, pugmill granulators, pour and crumble granulators, fluid-bed granulators, prill towers, and other forms of solid forming operations. The process is designed such that only minimal alterations are required to most every large (equal to or greater than 5 tons/hr) granulation plant now in operation which produce granules or prills of urea, monoammonium phosphate, diammonium phosphate, sulfur, ammonium sulfate, and ammonium nitrate, potassium nitrate, calcium nitrate, potassium phosphate, sodium nitrate, and mixtures of these products and others.

The following examples show how the present invention has taken the above concepts and developed them into a unique extended release agricultural product and method of making and using same.

Thus, the invention is demonstrated with reference to the following examples, which are of an illustrative nature only and which are to be construed as non-limiting.

EXAMPLE 1

Samples of controlled release urea were granulated using an 85% urea solution, with and without corn starch equal to 1% of the final product, and pre-heated perlite 3-S. The urea and corn starch were combined in a laboratory beaker. A laboratory scale homogenizer was used to evenly disperse the corn starch in the urea solution. In separate tests, a sufficient amount of perlite, both pre-heated to 300° F. and un-heated, was added to the urea/corn starch mixture to obtain almost complete absorption of the mixture. The mixture was removed from the beaker and allowed to solidify. Once the mixture had solidified and cooled, it was crumbled using a laboratory blender on the chop setting, and then screened to obtain −6+7 Tyler mesh (3.4 mm to 2.8 mm in diameter) fertilizer granules. These granules were then dried in a laboratory fluid-bed. The resulting materials were evaluated by placing 1 gm of sample in a test tube with 6 grams of water held at 75° F. for 1, 2, and 3 days, at which time the samples were drawn out of the test tube using a pipette after rotating the test tube end on end three times to create a homogenous solution. Urea retention in the perlite in all cases was over 250% better when it contained 1% corn starch instead of no corn starch and at least 35% better in all cases when the perlite was heated.

EXAMPLE 2

A pilot plant was set-up where urea was melted by a steam tube melter then blended with water to make an 85% solution and continuously fed at 109 lb/hr to a mix tank equipped with a homogenizer where corn starch powder was added at the rate of 1 lb/hr. The urea solution and the mix tank were maintained at a temperature of 210° F. Expanded 3-S perlite was continuously fed to a fluid-bed pre-heater at 7 lb/hr where it was heated with air until it was 320° F. to 327° F. (No water was applied to the perlite before hand and no steam was used to exfoliate it.) The perlite and the urea/corn starch mixture were then fed to a pugmill where most of the urea/corn starch mixture was absorbed while being held at a temperature of 196–197° F. The resulting slurry of perlite containing urea and corn starch plus excess urea and corn starch mixture was fed to a second pugmill. Oversize granules produced during the pilot plant operation were milled utilizing a Jacobson knife-bladed hammermill to obtain additional product size material and recycle. Recycle was added to the pugmill at a rate slightly over 2.5 to 1 that of the product made. The temperature of product leaving the pugmill was 136° F. The product and recycle were rounded and pre-dried in a rotating drum at 130° F. after which the product was dried in a fluid-bed dryer using 140° F. air.

The resulting product had a bulk density of 26 lb/ft$^3$, a perlite content of 8.8%, and a corn starch concentration of 1% giving a nitrogen content of 41.5+%; which resulted in a 9 hour dissolution rate in the aforementioned soil test of 43%, 23% after 24 hours, and 10% after 3 days.

EXAMPLE 3

Eighteen (18) grams of expanded 3-S perlite was placed in a laboratory vessel having an agitator and small vent. 20 ml of water were added to the vessel and mixed with the perlite, and it was heated so that it steamed for 1 hour at 220° F. 350 grams of a mixture of 85% urea solution with 1% of corn starch homogenized with it was added to the steaming perlite and mixed well. The mixture was poured onto a plastic surface to harden and then crumbled in a lab blender. The crumbled material was screened to −6+10 Tyler mesh (3.4 mm to 1.7 mm in diameter) and dried in a lab fluid-bed. The resulting material had a bulk density of 35 lb/ft$^3$. The material was then placed in a rotating drum and rounded by blowing hot air on it at 240° F. The bulk density of the resulting material was 38 lb/ft$^3$.

EXAMPLE 4

Eighteen (18) grams of expanded 3-S perlite was placed in a laboratory vessel and treated in the same manner as Example II except 350 grams of a 95% urea-1% corn starch mixture was added to the steaming perlite and mixed well. After crumbling, screening, and drying, the resulting material had a bulk density of 35 lb/ft$^3$ and after rounding, a bulk density of 37 lb/ft$^3$.

EXAMPLE 5

The same test was performed as Example 3, but a 98% urea-1% corn starch mixture was added to the steaming perlite. The resulting material had a bulk density of 38 lb/ft$^3$ and after rounding, a bulk density of 40 lb/ft$^3$.

EXAMPLE 6

The same test was performed as Example 3, but a pure urea melt was added to the 18 grams of steam perlite resulting in a bulk density of 41 lb/ft$^3$ and after rounding 43 lb/ft$^3$.

EXAMPLE 7

The apparatus of Example 2 was altered to allow additional exfoliation of the expanded perlite in order to get increased absorbency and increased bulk density per lab examples 3, 4, 5, and 6. The perlite was fed into a double shaft pugmill heated by a steam jacket at 85 psia or 316° F. The shafts were rotated at 130 rpm to give them a tip speed of 3.4 ft/sec. As the perlite was metered to the pugmill, it was moistened at the rate of approximately 1.1 grams of perlite per gram of water at the inlet end of the pugmill to allow absorption of the water into the perlite before the water was heated to the point of becoming steam. The water was applied through a tygon tube which dripped on the most active part of the bed in the pugmill. Retention time of the perlite in the pugmill was about 30 minutes. Photo micrographs showed the perlite exiting the pugmill to have enhanced exfoliation of the outer shell. The perlite was introduced to the urea/corn starch mixture in a second pugmill with its double shaft running at 72 rpm for a tip speed of 0.98 ft/sec. The temperature of the perlite-urea/corn starch mixture was controlled by a steam jacket at 271° F. through the use of 45 psia steam. The urea/corn starch mixture was prepared by melting granular urea and diluting it with water to 95% solution in the same mix tank as corn starch was homogenously blended into the mixture. The homogenizer operated at 3130 rpm and was powered by a 2 hp motor. The mixing was done in a semi-continuous manner. Residence time in the mixing tank was about 14 minutes during which it was under constant homogenization. Every 3 to 4 minutes, some of the mixture was withdrawn from the mixing vessel and put into a pump tank to provide continuous feed to the pugmill absorber. Once the withdrawal had occurred, additional amounts of urea and water to give a 95% urea solution were added to the mix vessel and corn starch was gradually poured into the vessel. The steam to the melter was 115 psia; however, temperatures of the mixing vessel was controlled at 269° F. In another change from Example 2, the perlite-urea/corn starch slurry leaving the absorber was sprayed by means of a steam eductor onto a rolling bed of granules in a rotating drum. The second pugmill mentioned in Example 2 was removed and the recycle and slurry were fed directly to the 4 ft dia. drum which was rotating at 15 rpm. Feed rate of urea @95% solution was 100.8 lb/hr with a corn starch feed rate of 1 lb/hr. Perlite fed at 4.2 lb/hr and recycle was fed back to the granulation drum at 27 lb/hr. Bed temperature within the granulation drum was controlled at 217° F. by means of blowing hot air at 227° F. onto the rotating bed. Material discharged by the drum was fed to a vibrating type screener for separation into product, oversize, and undersize. The undersize and oversize milled by a knife-bladed hammermill was fed back to the drum. Granulation was excellent, forming spherical granules and very little oversize. The product size granules of −6+10 Tyler mesh (3.4 mm to 1.7 mm in diameter) size were dried and found to have a bulk density of up to 43 lb/ft$^3$. In the soil burial tests previously mentioned, 33%, 16%, and 6% of the urea remained in the perlite after 9 hours, 24 hours, and 3 days, respectively. After drying the product, actual perlite content was 5.2% and corn starch was 1%. Nitrogen content of the product was 43+%. The hardness (crushing strength) of the urea by the recognized TVA crushing strength test as taught by TVA Bulletin Y-147 was 9+lbs of force for −6+7% Tyler mesh (3.4 mm to 2.8 mm in diameter) granules. Gel formation around and within the granules however, did not appear as good as the laboratory products when they were viewed as submerged in a watch glass filled with water and with a surface stereo microscope. The individual perlite particles separated to a larger extent than normal while in water rather than being bound together by the gel.

EXAMPLE 8

Using the same equipment as in Example 7 but with alterations to the operating conditions, the good gelling properties reappeared in the final product. The same feed rates were maintained as in Example 7 and the same method of operation was used for enhanced exfoliation. However, the pugmill rpm was reduced to 97 rpm and thus the tip speed was reduced to 2.5 ft/sec. The temperature maintained in the urea melting and corn starch homogenization steps were reduced; mix tank retention time was reduced to 3½ minutes and homogenization was reduced from 14 minutes to 1 minute. Temperatures in the mix tank were reduced to 258° F. and that in the pump tank to 262° F. The urea melt temperature fed to the mixing vessel was reduced to 283° F. and the pugmill absorber temperature was reduced to 266° F. The temperature to the perlite steaming pugmill was reduced to 313° F. Steam pressure in the slurry venturi nozzle was operated at 30 psig. The resulting bulk density of the −6+10 Tyler mesh product was 39 lb/ft$^3$. Urea remaining after 9 hours in the perlite after the soil burial tests was 44%, 10%, and 4.5% for 9 hours, 24 hours, and 3 days, respectively.

EXAMPLE 9

A 95% urea solution was homogenized to contain 1% corn starch and then for the most part absorbed by perlite equal to 4.5% of the final product in the same equipment as in Example 7. However, the granulation of the material was done by spreading the molten slurry onto the bed of the rotating drum by hand through use of a ice scoop of the open-top half-pipe style. The scoop allowed the material to be distributed across the rolling bed of the drum simulating a course spray discharge longitudinally across the rolling bed and falling curtains of particles as presently experienced in the large drum of a urea granulation plant. Otherwise the manner of operation was like that of Example 8. Urea melt at 100% and about 283° F. was fed to the mixing vessel. The mixture temperature was varied from 268° F. to 255° F. during the 4 hour operation as water and then corn starch was blended into it to make the aforementioned mixture. Feed rates for the urea, water, and corn starch were 111 lb/hr, 6 lb/hr, and 1 lb/hr respectively. There was essentially no heel left in the mix tank between blends. Once the blend was made, it was immediately discharged to the pump tank, thus providing continuous feed for the absorber. The urea/corn starch mixture was fed to the absorber along with the perlite which had been further exfoliated just prior to its introduction to the absorber. About 1 ml of H$_2$O per gram of perlite was introduced to the feed end of the pugmill and allowed to absorb into the perlite. It expanded into steam in the steam heated pugmill operating at 320° F., thus further exfoliating the perlite. The absorber was run at from 268° F. to 255° F. as the operation progressed. Slurry leaving the absorber was discharged to hand operated ice scoops. The granulation was done in the 4 ft diameter by 18' long drum rotating at 3.5 rpm, but increased to 7.5 rpm as the operation progressed. Some of the absorber discharge was put into a aluminum sheet and allowed to solidify in a slab. The drum recycle was 33 lb/hr and the temperature of the bed was maintained at between 192° F. to 201° F. using the recycle and the hot air blower for control. Material from the drum was screened to a product of −6+10 Tyler mesh and the oversize milled without drying and recycled to the screen. Undersize was fed to the drum as the recycle. As the temperature was varied in the homogenizer vessel from 268° F. to 255° F., the mixture changed from clear to opaque and the gel strength in the final product as observed by the stereo microscope increased significantly, as did the soil burial test results, which went from a urea retention in the perlite of 33% urea and 13% in 9 and 24 hours respectively, to a retention of 47% urea and 23% urea in the perlite in 9 and 24 hours respectively, as the test progressed. The bulk density was acceptable for the entire run but decreased with an increase in gel strength from 38 lb/ft$^3$ to 36.5 lb/ft$^3$.

EXAMPLE 10

The pilot plant of Example 9 was operated in the same manner and rates as the best means of Example 9. However, corn starch was applied at a strength of only 0.5% of the mixture. The resulting −6+10 Tyler mesh (3.4 mm to 1.7 mm in diameter) product had an increased bulk density of 39 lb/ft$^3$ and soil burial result showed 45%, 16%, and 6% of the urea retained after 9 hours, 24 hours, and 3 days respectively.

EXAMPLE 11

The pilot plant of Example 9 was operated in the same manner and rates as the best means of Example 9 except there was no addition of corn starch. Although the 95% solution of urea was absorbed by the perlite, it could not be granulated in the drum. The material was weak and turned to dust in the rotating drum. The perlite urea slurry was successfully poured out on an aluminum sheet and solidified as a slab. The material which was poured and solidified was milled into granules, but it created large quantities of dust and would be unacceptable in a plant operation.

EXAMPLE 12

A 95% urea solution was homogenized with corn starch to give a 6% corn starch product in the same manner as Example 1, but no perlite was added. The material was slowly poured on a bed of rotating granules in a pan granulator and granulated. The resulting product which contained no perlite was screened to −6+10 Tyler mesh (3.4 mm to 1.7 mm in diameter) product and had a bulk density of 32 lb/ft$^3$. In the soil burial, it had a urea retention of 27%, 15% and 6% in the solidified corn starch after 9 hours, 24 hours, and 3 days respectively.

EXAMPLE 13

The same test was done as above but had only 1% corn starch in the final product. The final product of −6+10 Tyler mesh (3.4 mm to 1.7 mm in diameter) granules had a bulk density of 40 lb/ft$^3$. In the soil burial tests, urea retention in the perlite was 10%, 3% and 1% after 9 hours, 24 hours, and 3 days respectively.

EXAMPLE 14

Using a standard pressure cooker, but without pressure development, expanded perlite was moistened with water at 20 ml of H$_2$O/18 grams of perlite in the laboratory and the vessel was heated to exfoliate the perlite. Urea containing the customary 0.3% to 0.5% formaldehyde used to condition it in most agricultural operations, was dissolved in H$_2$O to make a 95% solution. Corn starch was homogenized into the urea solution at 1% by weight. The urea/corn starch mixture was poured into the perlite such that the perlite content was 5% of the dried product and allowed to absorb the urea formaldehyde/corn starch mixture. The resulting material was poured onto an aluminum sheet to cool. Then it was crumbled with a laboratory blender on the chop cycle, screened to −6+10 Tyler mesh and dried. The resulting material had a bulk density of 33 lb/ft³ and in the soil burial test retained 51% urea, 31% urea, and 15% urea in the perlite after 9 hours, 24 hours, and 3 days respectively.

EXAMPLE 15

In the same manner as Example 14, material was produced in the laboratory where by urea, diammonium phosphate and potassium chloride were dissolved in water to make an 85% solution of the nutrients. The solution at 240° F. was added to perlite to contain 8% of the perlite which had been further expanded in the manner of Example 14. The resulting product had a nutrient content of 29% nitrogen, 3% $P_2O_5$, and 4% $K_2O$ and a bulk density of 41 lb/ft³. It showed excellent physical properties.

EXAMPLE 16

Established grass plots of 5 ft by 15 ft were all equally clipped on Aug. 15, 2000 to prepare for the application of fertilizers. On Aug. 16, 2000, the selected fertilizer blends were surface applied onto the individual plots. The fertilizer blends were as follows:

Commerical-1 Fertilizer (Vigoro) 29-3-4: derived from polymer coated urea; polymer coated sulfur coated urea, urea, diammonium phosphate, muriate of potash, ferrous sulfate, and ferric oxide and containing 7.3% slowly available urea nitrogen from polymer coated urea and polymer coated sulfur.

Urea based blend to make a 29-3-4 fertilizer containing:

| | |
|---|---|
| Urea = | 59.85% |
| Diammonium phosphate = | 6.55% |
| Muriate of potash = | 6.45% |
| Ferrous sulfate and ferric oxides = | 2.00% |
| Clay = | 4.2% |
| Limestone = | 20.95% |
| TOTAL = | 100.00% |

Commercial-2 Fertilizer (Scotts Turf Builder) 29-3-4: derived from monoammonium phosphate, urea, methylene ureas, muriate of potash and containing 8.7% slowly available methylene diurea and dimethylenetriurea nitrogen.

Urea-perlite- at 0.92% corn starch based blend to make a 29-3-4 fertilizer which consisted of the base of controlled release fertilizer as formulated to be:

| | |
|---|---|
| Urea: | 92.44% |
| Corn starch: | .92% |
| Perlite 3-S: | 6.64% |
| TOTAL: | 100.00% | and which made up 64.75% of the blend the remainder of the blend containing

| | |
|---|---|
| diammonium phosphate | 6.55% |
| muriate of potash | 6.45% |
| ferrous sulfate and ferric oxides | 2.00% |
| clay | 4.20% |
| limestone | 16.05% |
| TOTAL | 100.00% |

Urea-perlite- at 3.60% corn starch based blend to make a 29-3-4 fertilizer which consisted of the base of controlled release fertilizer as formulated to be:

| | |
|---|---|
| Urea: | 89.94% |
| Corn starch: | 3.60% |
| Perlite 3-S: | 6.46% |
| TOTAL: | 100.00% | and which made up 66.45% of the blend the remainder of the blend containing

| | |
|---|---|
| diammonium phosphate | 6.55% |
| muriate of potash | 6.45% |
| ferrous sulfate and ferric oxides | 2.00% |
| clay | 4.20% |
| limestone | 14.35% |
| TOTAL | 100.00% |

Figure 6:
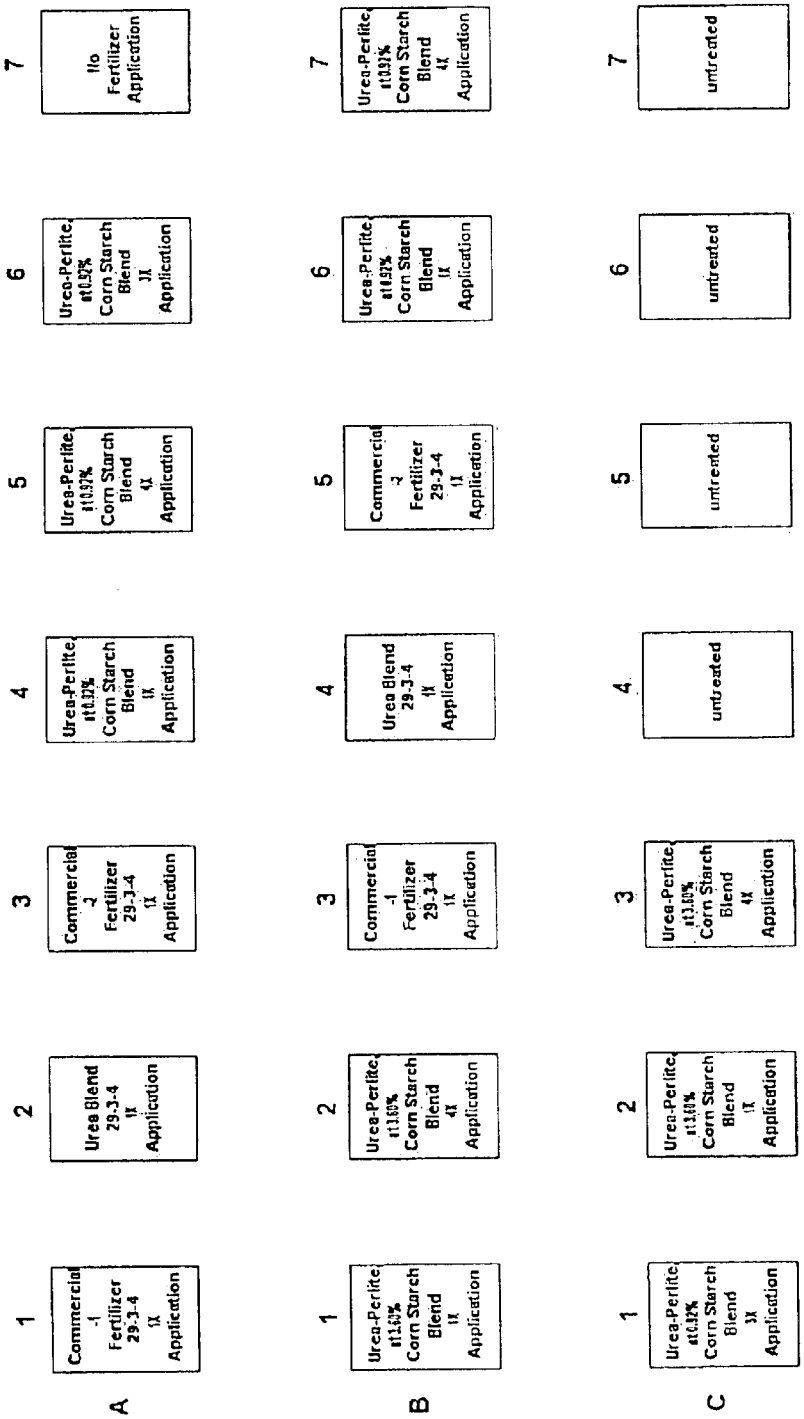
FIG. 6 is a schematic showing the plant growth test plots of Example 16, demonstrating the utility and effectiveness of the products of the present invention.

The application rate for the grass trials was 1 lb of nitrogen per 1000 ft² of surface based on the normal practice of the lawn care industry. Equal applications of phosphorus and potassium were contained in all the blends. Each application of fertilizer was replicated. The fertilizers were watered in moderately, immediately following the fertilizer application. The plot diagram in FIG. 6 shows the fertilizer applied by types, rates, and plot location. Three and four multiple rates of the urea perlite-0.92% corn starch and 3.60% corn starch containing fertilizers were applied to some plots as indicated on FIG. 6, to test leaf burning tendencies of the urea-perlite-corn starch products and to see the grass yield performance at the higher application rates.

The grass was cut on a 7 day interval. The grass cutting height was established at 3 inches. A moisture meter was used to determine irrigation requirements. Depending upon soil and atmosphere temperatures and humidity, the plots were irrigated as required, approximately three times weekly.

Visual observation and harvesting of the grass were two methods used to evaluate the performance of the controlled release fertilizer.

A greening rating of each plot was taken each Wednesday prior to cutting the grass and irrigating. The greening rating was based on a scale of 1 to 5 with 5 being the best possible and 1 the lowest rating. At the same time, the grass plots were examined for any indication of blade damage due to too much fertilizer availability.

The grass clippings were weighed after each cutting. One grass sample from each type of fertilized plot was analyzed for the nitrogen content each week.

The grass greening test data is shown by plots and fertilizer types and rates in Table 2. The first greening rating was made on Aug. 23, 2000 exactly one week after the fertilizer application was made on Aug. 16, 2000. The urea-perlite-0.92% corn starch and urea-perlite-3.60% corn starch based fertilizers produced a quick greening of the grass and continued to perform in an excellent manner until the killing frosts of October 8$^{th}$ and 9$^{th}$. In particular, the fertilizers containing the urea-perlite-0.92% corn starch based blend maintained an excellent rating and at the conclusion of the trial on Oct. 11, 2000, had an average rating of 3.27 on the A-4 plot and a 3.67 average rating on the B-6 plot. This was overall superior to any other tested fertilizer when applied at the rate of 1 lb for nitrogen per 1,000 ft$^2$ of surface. There was never any evidence of blade damage due to excessive availability of the fertilizer.

TABLE 2

GRASS PLOTS
GREENING TEST DATA[1,2,3,4]

| Plot # | Plot Description | Aug. 23, 2000 | Aug. 30, 2000 | Sep. 06, 2000 | Sep. 13, 2000 | Sep. 20, 2000 | Sep. 27, 2000 | Oct. 04, 2000 | Oct. 11, 2000 | SUM | AVG |
|---|---|---|---|---|---|---|---|---|---|---|---|
| A-1 | Commercial-1 Fertilizer 29-3-4 (1×) | 2.68 | 2.33 | 3.00 | 3.55 | 3.10 | 2.33 | 2.65 | 1.50 | 21.14 | 2.64 |
| A-2 | Urea Blend (29-3-4) (1×) | 2.93 | 2.50 | 2.93 | 3.68 | 3.00 | 2.35 | 2.65 | 1.50 | 21.54 | 2.69 |
| A-3 | Commercial-2 Fertilizer 29-3-4 (1×) | 2.73 | 2.45 | 2.80 | 3.68 | 3.05 | 2.25 | 2.30 | 1.50 | 20.76 | 2.60 |
| A-4 | Urea-Perlite, at 0.92% Corn Starch (29-3-4) (1×) | 3.23 | 3.95 | 4.08 | 4.23 | 3.65 | 2.85 | 2.65 | 1.50 | 26.14 | 3.27 |
| A-5 | Urea-Perlite, at 0.92% Corn Starch (29-3-4) (4×) | 4.45 | 4.43 | 4.55 | 4.68 | 4.13 | 3.32 | 3.20 | 1.50 | 30.26 | 3.78 |
| A-6 | Urea-Perlite, at 0.92% Corn Starch (29-3-4) (3×) | 3.50 | 4.20 | 4.65 | 4.68 | 4.25 | 3.45 | 3.30 | 1.50 | 29.53 | 3.69 |
| A-7 | No Fertilizer | 2.45 | 2.25 | 2.28 | 3.00 | 2.93 | 3.60 | 3.60 | 1.50 | 21.61 | 2.70 |
| B-1 | Urea-Perlite, at 3.60% Corn Starch (29-3-4) (1×) | 3.25 | 2.70 | 2.88 | 3.75 | 3.23 | 2.88 | 3.70 | 1.50 | 23.89 | 2.99 |
| B-2 | Urea-Perlite, at 3.60% Corn Starch (29-3-4) (4×) | 4.23 | 4.55 | 4.43 | 4.63 | 4.03 | 3.43 | 3.90 | 1.50 | 30.70 | 3.84 |
| B-3 | Commercial-1 Fertilizer 29-3-4 (1×) | 2.95 | 2.55 | 2.88 | 4.05 | 3.03 | 3.00 | 3.15 | 1.50 | 23.11 | 2.89 |
| B-4 | Urea Blend (29-3-4) (1×) | 3.00 | 4.03 | 3.78 | 4.05 | 3.65 | 3.18 | 3.25 | 1.50 | 26.44 | 3.31 |
| B-5 | Commercial-2 Fertilizer 29-3-4 (1×) | 2.88 | 4.18 | 4.00 | 4.05 | 3.58 | 3.23 | 3.13 | 1.50 | 26.55 | 3.32 |
| B-6 | Urea-Perlite, at 0.92% Corn Starch (29-3-4) (1×) | 3.75 | 4.33 | 4.30 | 4.38 | 3.83 | 3.50 | 3.80 | 1.50 | 29.39 | 3.67 |
| B-7 | Urea-Perlite, at 0.92% Corn Starch (29-3-4) (4×) | 4.48 | 4.75 | 4.93 | 4.85 | 4.15 | 4.00 | 4.30 | 1.50 | 32.96 | 4.12 |
| C-1 | Urea-Perlite, at 0.92% Corn Starch (29-3-4) (3×) | 4.00 | 4.20 | 4.33 | 4.55 | 4.00 | 3.52 | 4.00 | 1.50 | 30.10 | 3.76 |
| C-2 | Urea-Perlite, at 3.60% Corn Starch (29-3-4) (1×) | 3.63 | 3.98 | 4.13 | 4.35 | 3.35 | 2.95 | 3.90 | 1.50 | 27.79 | 3.47 |
| C-3 | Urea-Perlite, at 3.60% Corn Starch (29-3-4) (4×) | 4.25 | 4.60 | 4.80 | 4.75 | 4.13 | 3.48 | 3.90 | 1.50 | 31.41 | 3.93 |

Note
[1] A (1X) application rate is 1 pound of nitrogen per thousand square feet, 3X and 4X are 3 and 4 pounds of nitrogen per 1000 square feet respectively
[2] The ratings were made on seven day intervals
[3] Visual observation are on a scale of 1 to 5 (5 being the highest rating)
[4] Fertilizer application was applied on Aug. 16, 2000

The cumulative wet weight grass clipping weights for the replicated plots are shown in Table 3. The urea-perlite and 0.92% corn starch based blend at 1X application rate, at the conclusion of the trials on Oct. 11, 2000; had 97% more total weight produced than that produced by the urea based blend, 108% more than that produced by the Commerical-1 fertilizer 29-3-4 blend, and 48% more than that produced by the Commerical-2 fertilizer 29-3-4 blend. In addition, the urea-perlite-0.92% corn starch based blend maintained superior grass growth over the entire duration of the eight week test.

In Table 3, the first number is the combined weights and the second number is the cumulative weights. The no fertilizer plot did not have a replicated plot.

TABLE 3

GRASS CLIPPING DATA(GRAMS)[1,2,3,4,5,6,7,8]

| PLOT DESCRIPTION[9,10] | Aug. 23, 2000 | Aug. 30, 2000 | Sep. 06, 2000 | Sep. 13, 2000 | Sep. 20, 2000 | Sep. 27, 2000 | Oct. 04, 2000 | Oct. 11, 2000 |
|---|---|---|---|---|---|---|---|---|
| ZERO FERTILIZER | 15 | 54/69 | 38/107 | 66/173 | 53/226 | 54/280 | 18/298 | 6/304 |
| UREA (29-3-4) (1×) | 82 | 192/274 | 215/489 | 270/759 | 102/861 | 101/962 | 53/1015 | 13/1028 |
| COMMERCIAL-1 FERTILIZER (29-3-4) (1×) | 65 | 150/215 | 198/413 | 266/629 | 147/776 | 142/918 | 48/966 | 6/972 |

TABLE 3-continued

GRASS CLIPPING DATA(GRAMS)[1,2,3,4,5,6,7,8]

| PLOT DESCRIPTION[9,10] | Aug. 23, 2000 | Aug. 30, 2000 | Sep. 06, 2000 | Sep. 13, 2000 | Sep. 20, 2000 | Sep. 27, 2000 | Oct. 04, 2000 | Oct. 11, 2000 |
|---|---|---|---|---|---|---|---|---|
| COMMERCIAL-2 LAWN FERTILIZER 29-3-4 (1×) | 123 | 260/383 | 324/707 | 338/1045 | 162/1207 | 101/1308 | 60/1368 | 5/1373 |
| UREA-PERLITE, AT 0.92% CORN STARCH (29-3-4) (1×) | 228 | 481/709 | 497/1206 | 428/1634 | 145/1779 | 162/1941 | 75/2016 | 10/2026 |
| UREA-PERLITE, AT 0.92% CORN STARCH (29-3-4) (4×) | 487 | 1790/2277 | 1406/3683 | 1026/4709 | 465/5174 | 350/5524 | 79/5603 | 33/5636 |
| UREA-PERLITE, AT 0.92% CORN STARCH (29-3-4) (3×) | 66 | 600/666 | 1094/1760 | 919/2679 | 469/3148 | 264/3412 | 111/3523 | 23/3546 |
| UREA-PERLITE, AT 3.60% CORN STARCH (29-3-4) (1×) | 146 | 352/498 | 445/943 | 450/1393 | 142/1535 | 125/1660 | 81/1741 | 5/1746 |
| UREA-PERLITE, AT 3.60% CORN STARCH (29-3-4) (4×) | 449 | 1730/2179 | 1312/3491 | 1164/4655 | 322/4977 | 272/5249 | 167/5416 | 17/5433 |
| SOIL TEMPERATURE[4,5] | 72 | 69 | 75 | 65 | 66 | 61 | 57 | 52 |
| SOIL MOISTURE[7] | 7.4 | 7.0 | 7.0 | 7.4 | 8.8 | 10.0 | 9.0 | 9.0 |

NOTES:
[1]AVERAGE CLIPPING WEIGHTS FOR THE DUPLICATE PLOTS. THE CONTROL PLOT WAS NOT DUPLICATED.
[2]TEST PLOTS WERE FERTILIZED ON AUG. 16, 2000.
[3]LENGTH OF CUTTING INTERVAL = SEVEN DAYS
[4]HEIGHT OF CUTTING = 3 INCHES
[5]SOIL TEMPERATURE IN DEGREE FAHRENHEIT (AVERAGE OVER SEVEN DAY PERIOD)
[6]SOIL TEMPERATURE HAS A SIGNIFICANT CORRELATION ON 419 TIFTON BERMUDA GRASS GROWTH.
[7]CUMMULATIVE WEIGHT FOLLOWS WEIGHT OF CLIPPINGS FOR EACH DATE.
[8]SOIL MOISTURE WAS MAINTAINED BETWEEN 7 AND 10 UTILIZING A SOIL MOISTURE METER.
[9]REFERS TO BASE MATERIAL USED IN THE N-P-K BLEND WHICH WAS APPLIED TO THE DUPLICATE PLOTS
[10]ALL FERTILIZERS WERE BLENDED TO GIVE A 29-3-4 N-P-K ANALYSIS

The nitrogen concentration data by sample is shown in Table 4. Besides showing excellent total grass production on each cutting, the urea-perlite-0.92% corn starch blend at the base application rate of 1 lb per 1,000 ft² maintained excellent nitrogen content. The test results clearly indicate that the urea-perlite-0.92% and 3.60% corn starch blends provide the ability not only to quickly green and then maintain grass green while preventing blade burn damage, but they also allow tremendous increase in growth and nitrogen recovery by this grass and most likely many other grasses as well as other food and foliage producing vegetation.

TABLE 4

NITROGEN CONCENTRATION DATA BY PLOTS [1,2,3,4,5]

| Plot # | Plot Description | Aug. 23, 2000 | Aug. 30, 2000 | Sep. 06, 2000 | Sep. 13, 2000 | Sep. 20, 2000 | Sep. 27, 2000 | Oct. 04, 2000 |
|---|---|---|---|---|---|---|---|---|
| A-7 | No Fertilizer | 2.29% | 2.15% | 2.79% | 2.81% | 2.70% | 2.76% | 2.41% |
| B-3 | Commercial-1 Fertilizer 29-3-4 (1×) | 2.41% | 2.83% | 2.79% | 2.70% | 2.88% | 2.68% | 2.39% |
| B-4 | Urea Blend (29-3-4) (1×) | 2.50% | 3.02% | 3.25% | 2.87% | 3.05% | 2.67% | 2.48% |
| B-5 | Commercial-2 Fertilizer 29-3-4 (1×) | 2.73% | 3.19% | 3.05% | 2.82% | 3.00% | 2.73% | 2.47% |
| B-6 | Urea-Perlite, at 0.92% Corn Starch (29-3-4) (1×) | 3.46% | 3.57% | 3.22% | 3.20% | 3.02% | 3.13% | 2.85% |
| B-7 | Urea-Perlite, at 0.92% Corn Starch (29-3-4) (4×) | 4.20% | 4.38% | 4.19% | 3.90% | 3.24% | 3.91% | 3.66% |
| C-1 | Urea-Perlite, at 0.92% Corn Starch (29-3-4) (3×) | 3.35% | 4.34% | 3.70% | 3.60% | 3.53% | 3.39% | 3.12% |
| C-2 | Urea-Perlite, at 3.60% Corn Starch (29-3-4) (1×) | 3.10% | 3.31% | 3.07% | 3.02% | 3.11% | 2.87% | 2.67% |
| C-3 | Urea-Perlite, at 3.60% Corn Starch (29-3-4) (4×) | 3.85% | 4.18% | 4.09% | 3.75% | 3.93% | 3.50% | 3.34% |

Note
[1]Fertilizer application was applied on Aug. 16, 2000
[2]1× application rate represents 1 pound of nitrogen per thousand square feet
[3]Grass clippings from this duplicate test plot areas were analyzed for nitrogen content.
[4]Grass samples analyzed by Thornton Laboratories Tampa, Florida
[5]Grass clippings harvested on seven day intervals

EXAMPLE 17

In the same manner as Example 14, material was produced in the laboratory where by using a pressure cooker, but without pressure development, expanded perlite was moistened with water at 20 ml of $H_2O$ per 18 grams of perlite in the laboratory and vessel was heated to exfoliate the perlite. Urea was dissolved in $H_2O$ to make a 95% solution. Unmodified wheat starch was homogenized into the urea solution at 1% by weight. The urea/wheat starch mixture was poured into the exfoliated perlite such that the perlite content was 5.2% of the dried product and allowed to absorb the urea/wheat starch mixture. The resulting material was poured onto an aluminum sheet to cool. Then it was crumbled with a laboratory blender on the chop cycle, screened to −6+10 Tyler mesh and dried. The resulting material had a bulk density of 33 lb/ft$^3$ and in soil burial tests, retained 61% of the urea after 9 hours and 30% after 24 hours.

EXAMPLE 18

Urea was dissolved in $H_2O$ to make a 95% solution. Corn starch was homogenized into the urea solution at 1% by weight. The urea/corn starch mixture was poured into a vessel containing newspaper which had been chopped in a laboratory blender to a near lint condition. The newspaper was not steamed, wetted, or pre-heated before being exposed to the urea/corn starch mixture. The newspaper content was 3.5% of the final product. The resulting material was poured on an aluminum sheet to cool. Then it was crumbled with a laboratory blender on the chop cycle, screened to −6+10 Tyler mesh and dried. The resulting material had a bulk density of 30 lb/ft$^3$ and in a soil burial test, retained 46% of the urea after 9 hours and 17% of the urea after 24 hours.

EXAMPLE 19

Using a standard pressure cooker but without pressure development, expanded perlite was moistened with water at 20 ml of $H_2O$ per 36 grams of perlite in the laboratory and the vessel was heated to exfoliate the perlite. 700 grams of urea was dissolved in $H_2O$ along with 3 grams of magnesium oxide such that the solution became 85% urea. The solution was poured into the vessel containing the 36 gram of exfoliated perlite and mixed. The resulting material was poured onto an aluminum foil to harden. The hardened mixture was crumbled in the laboratory blender and screened to −6+10 Tyler mesh. The granules were dried. The bulk density was 28 lbs/ft$^3$.

EXAMPLE 20

A urea/corn starch homogenous mixture was prepared in the laboratory using a 95% solution of urea and homogenizing corn starch into the urea solution at 265° F. to make a mixture containing 8% corn starch. The mixture was poured onto a metal pan and allowed to solidify after which it was crumbled using a laboratory blender on the chop cycle, screened, and dried. In the soil burial test, 62% of the urea remained in the corn starch gel after 9 hours. The products bulk density was 41 lb/ft$^3$.

EXAMPLE 21

In the same manner as Example 20, a mixture containing 6% corn starch was made and granulated by pouring it in a laboratory pan granulator. The resulting product was screened, dried, and soil tested. In the soil burial test, 25%, 21% and 15% of the original urea remained in the corn starch gel after 9 hours, 24 hours, and 3 days, respectively. The products bulk density was 32lb/ft$^3$.

While only a few exemplary embodiments of this invention have been described in detail, those skilled in the art will recognize that there are many possible variations and modifications which may be made in the exemplary embodiments while yet retaining many of the novel and advantageous features of this invention. Accordingly, it is intended that the following claims cover all such modifications and variations.

What is claimed is:

1. A controlled release agricultural absorbent based product comprising:
   particles of an absorbent material containing capillaries/voids between 10–200 microns in cross-sectional diameter which is impregnated in an amount of 40–95% of the capillaries/voids volume with an agriculturally beneficial material selected from the group consisting of fertilizers, insecticides, herbicides and fungicides, said particles of absorbent material being agglomerated into granules.

2. The controlled release agricultural absorbent based product of claim 1 wherein the particles are agglomerated into granules having a size of 0.2–25 mm in diameter.

3. The controlled release agricultural absorbent based product of claim 1 wherein the particles are agglomerated into granules having a size of 1–4 mm in diameter.

4. The controlled release agricultural absorbent based product of claim 1 wherein the absorbent material is selected from the group consisting of expanded perlite, shredded newspaper, saw dusts, cotton lint, ground corn cobs, corn cob flower, Metrecz absorbent and diatomaceous earth.

5. The controlled release agricultural absorbent based product of claim 1, wherein the capillaries and voids are between 40 and 100 microns in cross-sectional diameter.

6. The controlled release agricultural absorbent based product of claim 1, wherein the absorbent is impregnated in an amount of 70–95% wt of the agricultural beneficial material.

7. The controlled release agricultural absorbent based product of claim 1, wherein the absorbent particles are 100–1500 microns in diameter.

8. The controlled release agricultural absorbent based product of claim 1, wherein the absorbent particles are 150–1000 microns in diameter.

9. The controlled release agricultural absorbent based product of claim 1, wherein the fertilizer is secondary nutrients selected from the group consisting of sulfur, calcium and magnesium.

10. The controlled release agricultural absorbent based product of claim 1, wherein the fertilizer is micronutrients selected from the group consisting of boron, copper, iron, manganese, molybdenum and zinc.

11. The controlled release agricultural absorbent based product of claim 1, wherein the fertilizer is selected from the group consisting of nitrogen compounds, phosphorous compounds and potassium compounds.

12. The controlled release agricultural absorbent based product of claim 11, wherein the nitrogen compounds are selected from the group consisting of urea, ammonia, ammonium nitrate, ammonium sulfate, calcium nitrate, diammonium phosphate, monoammonium phosphate, potassium nitrate and sodium nitrate.

13. The controlled release agricultural absorbent based product of claim 11, wherein the phosphorous compounds are selected from the group consisting of diammonium phosphate, monoammonium phosphate, monopotassium phosphate, dipotassium phosphate, tetrapotassium pyrophosphate, and potassium metaphosphate.

14. The controlled release agricultural absorbent based product of claim 11, wherein the potassium compound is selected from the group consisting of potassium chloride, potassium nitrate, potassium sulfate, monopotassium phosphate, dipotassium phosphate, tetrapotassium pyrophosphate, and potassium metaphosphate.

15. The controlled release agricultural absorbent based product of claim 11, wherein the fertilizer contains nitrogen, phosphorous and potassium compounds in a ratio selected from the group consisting of 29-3-4, 16-4-8, 10-10-10, 15-5-10, 15-0-15, 22-3-14, 20-28-5 and 12-6-6.

16. The controlled release agricultural absorbent based product of claim 1, wherein the fertilizer is a growth regulator selected from the group consisting of potassium azide, 2 amino-4-chloro-6-methyl pyrimidine, N-2, 5-dicorphenyl succinamide, 4-amino-1, and 2,4-triazole hydrochloride.

17. The controlled release agricultural absorbent based product of claim 1, wherein the fertilizer is a nitrification regulator selected from the group consisting of 2-chloro-6 trichloromethyl)pyridine, sulfathiazole, dicyandiamide, thiourea, and guanylthiourea.

18. The controlled release agricultural absorbent based product of claim 1, wherein the insecticide is 0,0-diethyl O-(2-isopropyl-6 methyl-4 pyrimidinyl) phosphorothioate).

19. The controlled release agricultural absorbent based product of claim 1, wherein the herbicide is 2,4-dichlorophenoxyacetic acid.

20. The controlled release agricultural absorbent based product of claim 1, wherein the fungicide is ferric-di-methyl-dithiocarbamate.

21. A controlled release agricultural absorbent based product comprising:
a particulate absorbent material containing capillaries/voids between 10–200 microns in cross-sectional diameter which is impregnated in an amount of 40–95% of the capillaries/voids volume with a mixture of an interspatial blocker and an agriculturally beneficial material selected from the group consisting of fertilizers, insecticides, herbicides and fungicides, wherein the particles of particulate absorbent material are agglomerated into granules.

22. The controlled release agricultural absorbent based product of claim 21 wherein the interspatial blocker is a material selected from the group consisting of plant starches, protein gels, glues, gumming compositions, crystallizing compounds, gelling clays, and synthetic gel forming compounds.

23. The controlled release agricultural absorbent based product of claim 21 wherein the interspatial blocker is a starch selected from the group consisting of corn starch, rice starch, potato starch, wheat starch, tapioca starch, starch containing D-glucopyranose polymers, amylose and amylopectin, starch acetates, starch esters, starch ethers, starch phosphates.

24. The controlled release agricultural absorbent based product of claim 21 wherein the interspatial blocker is corn starch or wheat starch.

25. The controlled release agricultural absorbent based product of claim 21 wherein the starches are modified by acetylation, chlorination, acid hydrolysis or enzymatic action.

26. The controlled release agricultural absorbent based product of claim 21 wherein the interspatial blocker is a starch selected from the group consisting of starch acetates, starch esters, starch ethers and starch phosphates.

27. The controlled release agricultural absorbent based product of claim 21 wherein the interspatial blocker is a gelatin made by hydrolysis of collagen.

28. The controlled release agricultural absorbent based product of claim 21 wherein the interspatial blocker is a glue made from a material selected from the group consisting of collagen, casein, blood and vegetable protein.

29. The controlled release agricultural absorbent based product of claim 21 wherein the interspatial blocker is a gumming composition selected from the group consisting of cellulosics, rubber latex, gums, terpene resins, mucilages, asphalts, pitches and hydrocarbon resins.

30. The controlled release agricultural absorbent based product of claim 21 wherein the interspatial blocker is a crystallizing compound selected from the group consisting of sodium silicate, phosphate cements, calcium-oxide cements and hydraulic cements.

31. The controlled release agricultural absorbent based product of claim 21 wherein the interspatial blocker is a gelling clay.

32. The controlled release agricultural absorbent based product of claim 21 wherein the interspatial blocker is a synthetic gel forming compound selected from the group consisting of polysulfide sealants, polyethylene, isobutylene, polyamides, polyvinyl acetate, epoxy, phenolformaldehyde, urea formaldehyde, polyvinyl butyral, cyanoacrylates and silicone cements.

33. The controlled release agricultural absorbent based product of claim 21 wherein the interspatial blocker is present in an amount of 0.01–20% wt.

34. The controlled release agricultural absorbent based product of claim 21 wherein the interspatial blocker is present in an amount of 0.2–10% wt.

35. The controlled release agricultural absorbent based product of claim 21 wherein the interspatial blocker is present in an amount of 0.5–4% wt.

36. A controlled release agricultural absorbent based product comprising:
particles of expanded perlite as an absorbent material, containing capillaries/voids between 10–200 microns in cross-sectional diameter, which is impregnated in an amount of 40–95% of the capillaries/voids volume with an agriculturally beneficial material selected from the group consisting of fertilizers, insecticides, herbicides and fungicides, wherein the particles of expanded perlite are agglomerated into granules.

37. The controlled release agricultural absorbent based product of claim 36 wherein the particles are agglomerated into granules having a size of 0.2–25 mm in diameter.

38. The controlled release agricultural absorbent based product of claim 36 wherein the particles are agglomerated into granules having a size of 1–4 mm in diameter.

39. The controlled release agricultural absorbent based product of claim 36 wherein the perlite is exfoliated perlite.

40. The controlled release agricultural absorbent based product of claim 36 wherein the fertilizer is urea and the resulting absorbent contains 40–45% wt. nitrogen.

41. The controlled release agricultural absorbent based product of claim 36 wherein the fertilizer is urea and the resulting absorbent contains 43–44% wt. nitrogen.

42. The controlled release agricultural absorbent based product of claim 36 wherein the fertilizer is urea and the resulting absorbent has a bulk density of 25–43 lb/ft$^3$.

43. The controlled release agricultural absorbent based product of claim 36 wherein the fertilizer is urea and the resulting absorbent has a bulk density of 38–46 lb/ft$^3$.

44. A controlled release agricultural absorbent based product comprising:
particles of expanded perlite as an absorbent material, containing capillaries/voids between 10–200 microns in cross-sectional diameter, which is impregnated in an amount of 40–95% of the capillaries/voids volume with a mixture of an interspatial blocker and an agriculturally beneficial material selected from the group consisting of fertilizers, insecticides, herbicides and fungicides, wherein the particles of expanded perlite are agglomerated into granules.

45. The controlled release agricultural absorbent based product of claim 44 wherein the particles are agglomerated into granules having a size of 0.2–25 mm in diameter.

46. The controlled release agricultural absorbent based product of claim 44 wherein the particles are agglomerated into granules having a size of 1–4 mm in diameter.

47. A controlled release agricultural absorbent based product comprising:
particles of exfoliated perlite as an absorbent material, containing capillaries/voids between 10–200 microns in cross-sectional diameter, which is impregnated in an amount of 40–95% of the capillaries/voids volume with a mixture of an interspatial blocker and an agriculturally beneficial material selected from the group consisting of fertilizers, insecticides, herbicides and fungicides.

48. The controlled release agricultural absorbent based product of claim 47 wherein the particles are agglomerated into granules.

49. The controlled release agricultural absorbent based product of claim 47 wherein the particles are agglomerated into granules having a size of 0.2–25 mm in diameter.

50. The controlled release agricultural absorbent based product of claim 47 wherein the particles are agglomerated into granules having a size of 1–4 mm in diameter.

51. The controlled release agricultural absorbent based product of claim 47 wherein the exfoliated perlite has a loose weight density of 2–20 lb/ft$^3$.

52. The controlled release agricultural absorbent based product of claim 47 wherein the exfoliated perlite has a loose weight density of 2–6 lb/ft$^3$.

53. A controlled release agricultural absorbent based product comprising:
particulate exfoliated perlite as an absorbent material, containing capillaries/voids between 10–200 microns in cross-sectional diameter, which is impregnated in an amount of 40–95% of the capillaries/voids volume with a mixture of a vegetable starch and an agriculturally beneficial material selected from the group consisting of fertilizers, insecticides, herbicides and fungicides, said particles of exfoliated perlite being agglomerated into granules.

54. The controlled release agricultural absorbent based product of claim 53 wherein the granules have a size of 0.2–25 mm in diameter.

55. The controlled release agricultural absorbent based product of claim 53 wherein the granules have a size of 1–4 mm in diameter.

56. The controlled release agricultural absorbent based product of claim 53, wherein the fertilizer is selected from the group consisting of nitrogen compounds, phosphorous compounds and potassium compounds.

57. The controlled release agricultural absorbent based product of claim 56, wherein the nitrogen compounds are selected from the group consisting of urea, ammonia, ammonium nitrate, ammonium sulfate, calcium nitrate, diammonium phosphate, monoammonium phosphate, potassium nitrate and sodium nitrate.

58. The controlled release agricultural absorbent based product of claim 56, wherein the phosphorous compounds are selected from the group consisting of diammonium phosphate, monoammonium phosphate, monopotassium phosphate, dipotassium phosphate, tetrapotassium pyrophosphate, and potassium metaphosphate.

59. The controlled release agricultural absorbent based product of claim 56, wherein the potassium compound is selected from the group consisting of potassium chloride, potassium nitrate, potassium sulfate, monopotassium phosphate, dipotassium phosphate, tetrapotassium pyrophosphate, and potassium metaphosphate.

60. The controlled release agricultural absorbent based product of claim 56, wherein the fertilizer contains nitrogen, phosphorous and potassium compounds in a ratio selected from the group consisting of 29-3-4, 16-4-8, 10-10-10, 15-5-10, 15-0-15, 22-3-14, 20-28-5 and 12-6-6.

61. The controlled release agricultural absorbent based product of claim 53 wherein the fertilizer is urea and the resulting absorbent contains 40–45% wt. nitrogen.

62. The controlled release agricultural absorbent based product of claim 53 wherein the fertilizer is urea and the resulting absorbent contains 43–44% wt. nitrogen.

63. The controlled release agricultural absorbent based product of claim 53 wherein the fertilizer is urea and the resulting absorbent has a bulk density of 25–43 lb/ft$^3$.

64. The controlled release agricultural absorbent based product of claim 53 wherein the fertilizer is urea and the resulting absorbent has a bulk density of 38–46 lb/ft$^3$.

65. The controlled release agricultural absorbent based product of claim 53 wherein the vegetable starch is present in an amount of 0.01–20% wt.

66. The controlled release agricultural absorbent based product of claim 53 wherein the vegetable starch is present in an amount of 2–8% wt.

67. The controlled release agricultural absorbent based product of claim 53 wherein the vegetable starch is present in an amount of 0.5–4% wt.

68. The controlled release agricultural absorbent based product of claim 53 wherein the vegetable starch is selected from the group consisting of corn starch, rice starch, potato starch, wheat starch and tapioca starch.

69. The controlled release agricultural absorbent based product of claim 53 wherein the vegetable starch is corn starch or wheat starch.

70. The controlled release agricultural absorbent based product of claim 53 wherein the perlite is impregnated in an amount of 60–90% of the capillaries/voids volume.

71. The controlled release agricultural absorbent based product of claim 53 wherein the perlite is impregnated in an amount of 80–90% of the capillaries/voids volume.

72. The controlled release agricultural absorbent based product of claim 53 wherein the exfoliated perlite has a loose weight density of 2–20 lb/ft$^3$.

73. The controlled release agricultural absorbent based product of claim 53 wherein the exfoliated perlite has a loose weight density of 2–6 lb/ft$^3$.

74. The controlled release agricultural absorbent based product of claim 53 wherein the hardness of the granules is 8–10 lbs of force for granules of 2.8–3.4 mm diameter.

75. The controlled release agricultural absorbent based product of claim 53 wherein the hardness of the granules is 0.9–1.1 lbs of force to 11–14 lbs of force for granules of 1–4 mm diameter.

76. The controlled release agricultural absorbent based product of claim 53, wherein the fertilizer is secondary nutrients selected from the group consisting of sulfur, calcium and magnesium.

77. The controlled release agricultural absorbent based product of claim 53, wherein the fertilizer is micronutrients selected from the group consisting of boron, copper, iron, manganese, molybdenum and zinc.

78. The controlled release agricultural absorbent based product of claim 53, wherein the fertilizer is a growth regulator selected from the group consisting of potassium azide, 2 amino-4-chloro-6-methyl pyrimidine, N-2, 5-dicorphenyl succinamide, 4-amino-1, and 2,4-triazole hydrochloride.

79. The controlled release agricultural absorbent based product of claim 53, wherein the fertilizer is a nitrification regulator selected from the group consisting of 2-chloro-6 trichloromethyl)pyridine, sulfathiazole, dicyandiamide, thiourea, and guanylthiourea.

80. The controlled release agricultural absorbent based product of claim 53, wherein the insecticide is 0,0-diethyl O-(2-isopropyl-6 methyl-4 pyrimidinyl) phosphorothioate).

81. The controlled release agricultural absorbent based product of claim 53, wherein the herbicide is 2,4-dichlorophenoxyacetic acid.

82. The controlled release agricultural absorbent based product of claim 53, wherein the fungicide is ferric-di-methyl-dithiocarbamate.

83. A process for preparing a controlled release agricultural absorbent based product comprising the following steps:
   introducing a predetermined amount of water to particles of absorbent material containing capillaries/voids between 10–200 microns in cross-sectional diameter, to result in absorption of water within the absorbent material;
   heating the absorbent particles and water to transform the water within the absorbent particles to steam;
   introducing the heated absorbent particles to an agriculturally beneficial material in aqueous solution selected from the group consisting of fertilizers, insecticides, herbicides and fungicides for blending to essentially saturate the absorbent particles with the agriculturally beneficial material;
   granulating the combination of agriculturally beneficial material and saturated absorbent particles to solidify and harden the mixture within the absorbent particles and outside the particles, resulting in the agglomeration of absorbent particles into granules; and
   drying the granules.

84. The process of claim 83 wherein the combination of agriculturally beneficial material and saturated absorbent particles is heated while blending.

85. The process of claim 83 wherein the granulated combination of agriculturally beneficial material and saturated absorbent particles is screened to result in granules of a predetermined diameter.

86. The controlled release agricultural absorbent based product of claim 83 wherein the granules have a size of 0.2–25 mm in diameter.

87. The process of claim 83 wherein undersized particles result from the screening step and are recycled back to the granulator where they agglomerate among themselves and among the incoming combination of agriculturally beneficial material and saturated absorbent particles.

88. The process of claim 83 wherein the combination of agriculturally beneficial material and saturated absorbent particles is introduced into the granulator by spraying means.

89. The process of claim 83 wherein the heating of the absorbent particles and water occurs in a heat exchanger.

90. The process of claim 83 wherein the combination of agriculturally beneficial material and saturated absorbent particles are solidified and hardened by a loss of heat and/or increase of concentration of the agriculturally beneficial material.

91. The process of claim 83 wherein the absorbent material is selected from the group consisting of expanded perlite, shredded newspaper, saw dusts, cotton lint, ground corn cobs, corn cob flower, Metrecz absorbent and diatomaceous earth.

92. The process of claim 83, wherein the absorbent is impregnated in an amount of 70–95% wt of the agricultural beneficial material.

93. The process of claim 83, wherein the fertilizer is secondary nutrients selected from the group consisting of sulfur, calcium and magnesium.

94. The process of claim 83, wherein the fertilizer is micronutrients selected from the group consisting of boron, copper, iron, manganese, molybdenum and zinc.

95. The process of claim 83, wherein the fertilizer is selected from the group consisting of nitrogen compounds, phosphorous compounds and potassium compounds.

96. The process of claim 95, wherein the nitrogen compounds are selected from the group consisting of urea, ammonia, ammonium nitrate, ammonium sulfate, calcium nitrate, diammonium phosphate, monoammonium phosphate, potassium nitrate and sodium nitrate.

97. The process of claim 95, wherein the phosphorous compounds are selected from the group consisting of diammonium phosphate, monoammonium phosphate, monopotassium phosphate, dipotassium phosphate, tetrapotassium pyrophosphate, and potassium metaphosphate.

98. The process of claim 95, wherein the potassium compound is selected from the group consisting of potassium chloride, potassium nitrate, potassium sulfate, monopotassium phosphate, dipotassium phosphate, tetrapotassium pyrophosphate, and potassium metaphosphate.

99. The process of claim 95, wherein the fertilizer contains nitrogen, phosphorous and potassium compounds in a ratio selected from the group consisting of 29-3-4, 16-4-8, 10-10-10, 15-5-10, 15-0-15, 22-3-14, 20-28-5 and 12-6-6.

100. The process of claim 83, wherein the fertilizer is a growth regulator selected from the group consisting of potassium azide, 2 amino-4-chloro-6-methyl pyrimidine, N-2, 5-dicorphenyl succinamide, 4-amino-1, and 2,4-triazole hydrochloride.

101. The process of claim 83, wherein the fertilizer is a nitrification regulator selected from the group consisting of 2-chloro-6 trichloromethyl)pyridine, sulfathiazole, dicyandiamide, thiourea, and guanylthiourea.

102. The controlled release agricultural absorbent based product of claim 83, wherein the insecticide is 0,0-diethyl O-(2-isopropyl-6 methyl-4 pyrimidinyl) phosphorothioate).

103. The controlled release agricultural absorbent based product of claim 83, wherein the herbicide is 2,4-dichlorophenoxyacetic acid.

104. The controlled release agricultural absorbent based product of claim 83, wherein the fungicide is ferric-di-methyl-dithiocarbamate.

105. The process of claim 83 wherein the absorbent material is particles of perlite and the step of heating the absorbent particles and water to transform the water within the absorbent particles to steam, acts to exfoliate the perlite for improved subsequent adsorption of the agriculturally beneficial material.

106. The process of claim 83 wherein the exfoliated perlite has a loose weight density of 2–20 lb/ft$^3$.

107. The process of claim 83 wherein the exfoliated perlite has a loose weight density of 2–6 lb/ft$^3$.

108. A process for preparing a controlled release agricultural absorbent based product comprising the following steps:
   introducing a predetermined amount of water to particles of absorbent material containing capillaries/voids between 10–200 microns in cross-sectional diameter, to result in absorption of water within the absorbent material;

heating the absorbent particles and water to transform the water within the absorbent particles to steam;

mixing an interspatial blocker material and an agriculturally beneficial material in aqueous solution selected from the group consisting of fertilizers, insecticides, herbicides and fungicides;

introducing the heated absorbent particles to the mixture of agriculturally beneficial material and interspatial blocker for blending and for absorption by the absorbent particles of the mixture of agriculturally beneficial material and interspatial blocker;

granulating the combination of agriculturally beneficial material, interspatial blocker and absorbent particles to solidify and harden the mixture within the absorbent particles and outside the particles, resulting in the agglomeration of absorbent particles into granules; and drying the granules.

109. The process of claim 108 wherein the interspatial blocker is a material selected from the group consisting of plant starches, protein gels, glues, gumming compositions, crystallizing compounds, gelling clays, and synthetic gel forming compounds.

110. The process of claim 108 wherein the interspatial blocker is a starch selected from the group consisting of corn starch, rice starch, potato starch, wheat starch, tapioca starch, starch containing D-glucopyranose polymers, amylose and amylopectin, starch acetates, starch esters, starch ethers, starch phosphates.

111. The process of claim 108 wherein the interspatial blocker is corn starch or wheat starch.

112. The process of claim 108 wherein the starches are modified by acetylation, chlorination, acid hydrolysis or enzymatic action.

113. The process of claim 108 wherein the interspatial blocker is a starch selected from the group consisting of starch acetates, starch esters, starch ethers and starch phosphates.

114. The process of claim 108 wherein the interspatial blocker is a gelatin made by hydrolysis of collagen.

115. The process of claim 108 wherein the interspatial blocker is a glue made from a material selected from the group consisting of collagen, casein, blood and vegetable protein.

116. The process of claim 108 wherein the interspatial blocker is a gumming composition selected from the group consisting of cellulosics, rubber latex, gums, terpene resins, mucilages, asphalts, pitches and hydrocarbon resins.

117. The process of claim 108 wherein the interspatial blocker is a crystallizing compound selected from the group consisting of sodium silicate, phosphate cements, calcium-oxide cements and hydraulic cements.

118. The process of claim 108 wherein the interspatial blocker is a synthetic gel forming compound selected from the group consisting of polysulfide sealants, polyethylene, isobutylene, polyamides, polyvinyl acetate, epoxy, phenolformaldehyde, urea formaldehyde, polyvinyl butyral, cyanoacrylates and silicone cements.

119. The process of claim 108 wherein the interspatial blocker is a gelling clay.

120. The process of claim 108 wherein the interspatial blocker is present in an amount of 0.01–20% wt.

121. The process of claim 108 wherein the interspatial blocker is present in an amount of 0.5–6% wt.

122. The process of claim 108 wherein the combination of agriculturally beneficial material and saturated absorbent particles is heated while blending.

123. The process of claim 108 wherein the granulated combination of agriculturally beneficial material and saturated absorbent particles is screened to result in granules of a predetermined diameter.

124. The process of claim 108 wherein the granules have a size of 0.2–25 mm in diameter.

125. The process of claim 108 wherein undersized particles result from the screening step and are recycled back to the granulator where they agglomerate among themselves and among the incoming combination of agriculturally beneficial material and saturated absorbent particles.

126. The process of claim 108 wherein the combination of agriculturally beneficial material and saturated absorbent particles is introduced into the granulator by spraying means.

127. The process of claim 108 wherein the heating of the absorbent particles and water occurs in a heat exchanger.

128. The process of claim 108 wherein the combination of agriculturally beneficial material and saturated absorbent particles are solidified and hardened by a loss of heat and/or increase of concentration of the agriculturally beneficial material.

129. The process of claim 108 wherein the absorbent material is selected from the group consisting of expanded perlite, shredded newspaper, saw dusts, cotton lint, ground corn cobs, corn cob flower, Metrecz absorbent and diatomaceous earth.

130. The process of claim 108 wherein the absorbent material is particles of perlite and the step of heating the absorbent particles and water to transform the water within the absorbent particles to steam, acts to exfoliate the perlite for improved subsequent adsorption of the agriculturally beneficial material.

131. The process of claim 108, wherein the absorbent is impregnated in an amount of 70–95% wt of the agricultural beneficial material.

132. The process of claim 108, wherein the fertilizer is secondary nutrients selected from the group consisting of sulfur, calcium and magnesium.

133. The process of claim 108, wherein the fertilizer is micronutrients selected from the group consisting of boron, copper, iron, manganese, molybdenum and zinc.

134. The process of claim 108, wherein the fertilizer is selected from the group consisting of nitrogen compounds, phosphorous compounds and potassium compounds.

135. The process of claim 134, wherein the nitrogen compounds are selected from the group consisting of urea, ammonia, ammonium nitrate, ammonium sulfate, calcium nitrate, diammonium phosphate, monoammonium phosphate, potassium nitrate and sodium nitrate.

136. The process of claim 134, wherein the phosphorous compounds are selected from the group consisting of diammonium phosphate, monoammonium phosphate, monopotassium phosphate, dipotassium phosphate, tetrapotassium pyrophosphate, and potassium metaphosphate.

137. The process of claim 134, wherein the potassium compound is selected from the group consisting of potassium chloride, potassium nitrate, potassium sulfate, monopotassium phosphate, dipotassium phosphate, tetrapotassium pyrophosphate, and potassium metaphosphate.

138. The process of claim 134, wherein the fertilizer contains nitrogen, phosphorous and potassium compounds in a ratio selected from the group consisting of 29-3-4, 16-4-8, 10-10-10, 15-5-10, 15-0-15, 22-3-14, 20-28-5 and 12-6-6.

139. The process of claim 108, wherein the fertilizer is a growth regulator selected from the group consisting of potassium azide, 2 amino-4-chloro-6-methyl pyrimidine, N-2, 5-dicorphenyl succinamide, 4-amino-1, and 2,4-triazole hydrochloride.

140. The process of claim 108, wherein the fertilizer is a nitrification regulator selected from the group consisting of 2-chloro-6 trichloromethyl)pyridine, sulfathiazole, dicyandiamide, thiourea, and guanylthiourea.

141. The process of claim 108, wherein the insecticide is 0,0-diethyl O-(2-isopropyl-6 methyl-4 pyrimidinyl) phosphorothioate).

142. The process of claim 108, wherein the herbicide is 2,4-dichlorophenoxyacetic acid.

143. The process of claim 108, wherein the fungicide is ferric-di-methyl-dithiocarbamate.

144. The process of claim 108, wherein the steps of combining water and the absorbent particles and then heating the combined absorbent particles and water to transform the water within the absorbent particles to steam are replaced by the step of directly introducing hot steam to the absorbent particles in order to produce absorbent particles containing steam.

145. A process for preparing a controlled release agricultural absorbent based product comprising the following steps:

introducing a predetermined amount of water to particles of expanded perlite as an absorbent material containing capillaries/voids between 10–200 microns in cross-sectional diameter, to result in absorption of water within the particles of expanded perlite;

exfoliating the particles of expanded perlite by heating the particles of expanded perlite and water to transform the water within the particles of expanded perlite to steam sufficient to rupture the outer surface of the particles of expanded perlite;

mixing an interspatial blocker material and an agriculturally beneficial material in aqueous solution selected from the group consisting of fertilizers, insecticides, herbicides and fungicides;

introducing the exfoliated particles of expanded perlite to the mixture of agriculturally beneficial material and interspatial blocker for blending and absorption of the mixture of agriculturally beneficial material and interspatial blocker by the particles;

granulating the combination of agriculturally beneficial material, interspatial blocker and absorbed exfoliated particles to solidify and harden the mixture within the absorbed particles and outside the particles, resulting in the agglomeration of particles into granules; and drying the granules.

146. A controlled release agricultural absorbent based product comprising:

a particulate absorbent material containing capillaries/voids between 10–200 microns in cross-sectional diameter which is impregnated in an amount of 40–95% of the capillaries/voids volume with a mixture of an interspatial blocker and an agriculturally beneficial material selected from the group consisting of fertilizers, insecticides, herbicides and fungicides, wherein the interspatial blocker is selected from the group consisting of plant starches, protein gels, collagen based glues, casein based glues, blood based glues, vegetable protein based glues, rubber latex, gums, terpene resins, mucilages, asphalts, pitches, hydrocarbon resins, sodium silicate, phosphate cements, calcium-oxide cements, hydraulic cements, gelling clays and synthetic gel forming compounds.

* * * * *